(12) United States Patent
Furst

(10) Patent No.: US 8,603,158 B2
(45) Date of Patent: Dec. 10, 2013

(54) IRRADIATED STENT COATING

(75) Inventor: Joseph G. Furst, Middlefield, OH (US)

(73) Assignee: Icon Interventional Systems, Inc, Cleveland, OH (US)

( * ) Notice: Subject to any disclaimer, the term of this patent is extended or adjusted under 35 U.S.C. 154(b) by 2975 days.

(21) Appl. No.: 10/810,356

(22) Filed: Mar. 26, 2004

(65) Prior Publication Data

US 2004/0181277 A1 Sep. 16, 2004

Related U.S. Application Data

(63) Continuation-in-part of application No. 09/771,073, filed on Jan. 29, 2001, now abandoned, which is a continuation-in-part of application No. 09/273,736, filed on Mar. 22, 1999, now Pat. No. 6,436,133, and a continuation-in-part of application No. 09/363,052, filed on Jul. 29, 1999, now Pat. No. 6,206,916.

(60) Provisional application No. 60/094,250, filed on Jul. 27, 1998, provisional application No. 60/081,824, filed on Apr. 15, 1998.

(51) Int. Cl.
*A61F 2/06* (2013.01)
*A61M 31/00* (2006.01)

(52) U.S. Cl.
USPC ......... 623/1.42; 623/1.15; 623/1.16; 604/509

(58) Field of Classification Search
USPC ............... 623/1.11, 1.15, 1.16, 1.42, 1.46; 427/261; 424/423; 514/44; 604/509
See application file for complete search history.

(56) References Cited

U.S. PATENT DOCUMENTS

| | | | |
|---|---|---|---|
| 4,733,665 A | 3/1988 | Palmaz |
| 4,739,762 A | 4/1988 | Palmaz |
| 4,776,337 A | 10/1988 | Palmaz |
| 4,888,389 A | 12/1989 | Kennedy et al. |
| 4,942,204 A | 7/1990 | Kennedy |
| 5,024,671 A | 6/1991 | Tu et al. |
| 5,051,272 A | 9/1991 | Hermes et al. |
| 5,059,166 A | 10/1991 | Fischell et al. |
| 5,067,491 A | 11/1991 | Taylor, II et al. |
| 5,073,381 A | 12/1991 | Ivan et al. |

(Continued)

FOREIGN PATENT DOCUMENTS

| | | |
|---|---|---|
| EP | 0 433 011 A1 | 6/1991 |
| EP | 0 836 839 A2 | 4/1998 |

(Continued)

OTHER PUBLICATIONS

Trapidil in Preventing Restenosis After Balloon Angioplasty in the Atherosclerotic Rabbit, Liu, et al., *Circulation*, vol. 81, No. 3, Mar. 1990.

(Continued)

*Primary Examiner* — Vy Q Bui
(74) *Attorney, Agent, or Firm* — Fay Sharpe LLP

(57) ABSTRACT

An expandable stent for use within a body passageway having a body member with two ends and a wall surface disposed between the ends. The body member has a first diameter to permit delivery of the body member into a body passageway and a second expanded diameter. The surface of the stent is coated with a biological agent and a polymer which controls the release of the biological agent.

44 Claims, 8 Drawing Sheets

(56) References Cited

U.S. PATENT DOCUMENTS

| | | |
|---|---|---|
| 5,102,417 A | 4/1992 | Palmaz |
| 5,108,424 A | 4/1992 | Hoffman, Jr. et al. |
| 5,180,366 A | 1/1993 | Woods |
| 5,185,408 A | 2/1993 | Tang et al. |
| 5,195,984 A | 3/1993 | Schatz |
| 5,197,977 A | 3/1993 | Hoffman, Jr. et al. |
| 5,246,452 A | 9/1993 | Sinnot |
| 5,263,349 A | 11/1993 | Felix et al. |
| 5,304,121 A | 4/1994 | Sahatijian |
| 5,306,250 A | 4/1994 | March et al. |
| 5,316,023 A | 5/1994 | Palmaz |
| 5,383,927 A | 1/1995 | De Goicoechea et al. |
| 5,383,928 A | 1/1995 | Scott et al. |
| 5,437,744 A | 8/1995 | Carlen |
| 5,443,498 A | 8/1995 | Fontaine |
| 5,449,382 A | 9/1995 | Dayton |
| 5,464,650 A | 11/1995 | Berg et al. |
| 5,500,013 A | 3/1996 | Buscemi et al. |
| 5,516,781 A | 5/1996 | Morris et al. |
| 5,545,208 A | 8/1996 | Wolff et al. |
| 5,563,146 A | 10/1996 | Morris et al. |
| 5,571,170 A | 11/1996 | Palmaz et al. |
| 5,578,075 A | 11/1996 | Dayton |
| 5,605,696 A | 2/1997 | Eury et al. |
| 5,609,629 A | 3/1997 | Fearnot et al. |
| 5,616,608 A | 4/1997 | Kinsella et al. |
| 5,624,411 A | 4/1997 | Tuch |
| 5,632,840 A | 5/1997 | Campbell |
| 5,649,977 A | 7/1997 | Campbell |
| 5,665,728 A | 9/1997 | Morris et al. |
| 5,679,400 A | 10/1997 | Tuch |
| 5,695,516 A | 12/1997 | Fischell et al. |
| 5,716,981 A | 2/1998 | Hunter et al. |
| 5,725,572 A | 3/1998 | Lam et al. |
| 5,733,303 A | 3/1998 | Israel et al. |
| 5,733,925 A | 3/1998 | Kunz et al. |
| 5,735,871 A | 4/1998 | Sgro |
| 5,755,781 A | 5/1998 | Jayaraman |
| 5,772,864 A | 6/1998 | Møller et al. |
| 5,776,183 A | 7/1998 | Kanesaka et al. |
| 5,807,944 A | 9/1998 | Hirt et al. |
| 5,824,045 A | 10/1998 | Alt |
| 5,824,049 A | 10/1998 | Ragheb et al. |
| 5,843,172 A | 12/1998 | Yan |
| 5,853,419 A | 12/1998 | Imran |
| 5,861,027 A | 1/1999 | Trapp |
| 5,879,370 A | 3/1999 | Fischell et al. |
| 5,911,732 A | 6/1999 | Hojeibane |
| 5,916,585 A | 6/1999 | Cook |
| 5,962,620 A | 10/1999 | Reich et al. |
| 5,964,798 A | 10/1999 | Imran |
| 5,968,091 A | 10/1999 | Pinchuk et al. |
| 5,981,568 A | 11/1999 | Kunz et al. |
| 5,993,972 A | 11/1999 | Reich et al. |
| 6,007,573 A | 12/1999 | Wallace et al. |
| 6,059,810 A | 5/2000 | Brown et al. |
| 6,066,325 A | 5/2000 | Wallace |
| 6,099,561 A | 8/2000 | Alt |
| 6,120,536 A | 9/2000 | Ding et al. |
| 6,146,358 A | 11/2000 | Rowe |
| 6,156,062 A | 12/2000 | McGuinness |
| 6,162,247 A | 12/2000 | Weadock et al. |
| 6,200,337 B1 | 3/2001 | Moriuchi et al. |
| 6,200,589 B1 | 3/2001 | Kennedy et al. |
| 6,200,960 B1 | 3/2001 | Khachigan |
| 6,206,916 B1 | 3/2001 | Furst |
| 6,221,099 B1 | 4/2001 | Andersen et al. |
| 6,240,616 B1 | 6/2001 | Yan |
| 6,258,121 B1 | 7/2001 | Yang et al. |
| 6,299,604 B1 | 10/2001 | Ragheb et al. |
| 6,335,029 B1 | 1/2002 | Kamath et al. |
| 6,358,556 B1 | 3/2002 | Ding et al. |
| 6,365,171 B1 | 4/2002 | Kennedy et al. |
| 6,368,658 B1 * | 4/2002 | Schwarz et al. ............. 427/2.15 |
| 6,391,052 B2 | 5/2002 | Buirge et al. |
| 6,399,144 B2 | 6/2002 | Dinh et al. |
| 6,419,692 B1 | 7/2002 | Yang et al. |
| 6,436,133 B1 | 8/2002 | Furst et al. |
| 6,515,009 B1 * | 2/2003 | Kunz et al. ..................... 514/411 |
| 6,517,571 B1 | 2/2003 | Brauker et al. |
| 6,528,584 B2 | 3/2003 | Kennedy et al. |
| 6,555,619 B1 | 4/2003 | Kennedy et al. |
| 6,583,251 B1 | 6/2003 | Chaikof et al. |
| 6,641,611 B2 | 11/2003 | Jayaraman |
| 6,695,833 B1 | 2/2004 | Frantzen |
| 6,726,923 B2 | 4/2004 | Lyer et al. |
| 2001/0013166 A1 | 8/2001 | Yan |
| 2001/0014717 A1 | 8/2001 | Hossainy et al. |
| 2002/0032414 A1 | 3/2002 | Ragheb et al. |
| 2002/0051730 A1 | 5/2002 | Bodnar et al. |
| 2002/0054900 A1 | 5/2002 | Kamath et al. |
| 2002/0065546 A1 * | 5/2002 | Machan et al. ............. 623/1.13 |
| 2002/0082679 A1 * | 6/2002 | Sirhan et al. ................. 623/1.15 |
| 2002/0095133 A1 | 7/2002 | Gillis et al. |
| 2002/0098278 A1 | 7/2002 | Bates |
| 2003/0026840 A1 | 2/2003 | Plank et al. |
| 2003/0040790 A1 | 2/2003 | Furst |
| 2003/0064098 A1 | 4/2003 | Kararli et al. |
| 2003/0083646 A1 | 5/2003 | Sirhan et al. |
| 2003/0093141 A1 | 5/2003 | Dimatteo et al. |
| 2003/0099712 A1 | 5/2003 | Jayaraman |
| 2003/0199969 A1 | 10/2003 | Steinke et al. |
| 2003/0216534 A1 | 11/2003 | Chaikof et al. |
| 2003/0228364 A1 | 12/2003 | Nathan |
| 2003/0229390 A1 | 12/2003 | Ashton et al. |
| 2003/0229392 A1 | 12/2003 | Wong |
| 2003/0229393 A1 | 12/2003 | Kutryk et al. |
| 2004/0093076 A1 | 5/2004 | White et al. |
| 2004/0093077 A1 | 5/2004 | White et al. |

FOREIGN PATENT DOCUMENTS

| | | |
|---|---|---|
| JP | 5-123394 | 2/2011 |
| WO | WO 93/16176 | 8/1993 |
| WO | WO 99/49907 | 10/1999 |
| WO | WO 99/56663 A2 | 11/1999 |
| WO | WO 00/32255 | 6/2000 |
| WO | WO 00/66189 | 11/2000 |
| WO | WO 01/17577 A1 | 3/2001 |
| WO | WO 01/45763 | 6/2001 |
| WO | WO 01/56640 | 8/2001 |
| WO | WO 01/97964 | 12/2001 |

OTHER PUBLICATIONS

*DNA Delivery from Polymer Matrices for Tissue Engineering*, Shea, et al., Nature Biotechnology, vol. 17, Jun. 1999.

*Polymeric System for Dual Growth Factor Delivery*, Richardson, et al., Nature Biotechnology, vol. 19, Nov. 2001.

*Controlled Growth Factor Release from Synthetic Extracellular Matrices*, Lee, et al., Nature, vol. 408, Dec. 21/28, 2000.

*Progress in Cardiovascular Disease*, Sonnenblick, et al., Sep./Oct. 1996.

*USCI PE Plus Peripheral Balloon Dilatation Catheter* brochure.

*Results of a Meta-Analysis of Trapidil, a PDGF Inhibitor Â' A Sufficient Reason for a Second Look to the Pharmacological Approach to Restenosis*, Serruys PW, Banz K, Darcis T, Mignot A, van Es GA, Schwicker D., J Invasive Cardiol. Oct. 1997;9(8):505-512.

*A Randomized Comparison of Trapidil (triazolopyrimidine), a Platelet-Derived Growth Factor Antagonist, Versus Aspirin in Prevention of Angiographic Restenosis after Coronary Artery Palmaz-Schatz Stent Implantation*, Galassi AR, Tamburino C, Nicosia A, Russo G, Grassi R, Monaco A, Giuffrida G., Catheter Cardiovasc Interv. Feb. 1999;46(2):162-8.

*Reference Chart Derived From Post-Stent-Implantation Intravascular Ultrasound Predictors of 6-Month Expected Restenosis on Quantitative Coronary Angiography*, P. J. de Feyter, P. Kay, C. Disco, and P. W. Serruys, Circulation, Oct. 1999; 100: 1777-1783.

*Trapidil Inhibits Monocyte Chemoattractant Protein-1 and macrophage Accumulation After Balloon Arterial Injury in Rabbits*, Poon M, Cohen J, Siddiqui Z, et al., Lab Invest. 1999;79:1369-1375.

(56) References Cited

OTHER PUBLICATIONS

*The TRAPIST study—A multicentre randomized placebo controlled clinical trial of trapidil for prevention of restenosis after coronary stenting, measured by 3-D intravascular ultrasound*, P.W. Serruys, D.P. Foley, M. Pieper, J.A. de Feyter on behalf of the TRAPIST investigators, European Heart Journal (2001) 22, 1938-1947, doi:10.1053/euhj.2001.2627, available online at http://www.idealibrary.com.

Abstract of *Pharmacological Properties of Trapidil: Comparison with Other Coronary Vasodilators*, Ohnishi H, Kosuzume H, Yamaguchi K, Sato M, Umehara S, Funato H, Itoh C, Suzuki K, Kitamura Y, Suzuki Y, Itoh R., Nippon Yakurigaku Zasshi. Sep. 1980;76(6):495-503.

Abstract of *Effects of Trapidil on Thromboxane A2-induced Aggregation of Platelets, Ischemic Changes in Heart and Biosynthesis of Thromboxane A2*, Ohnishi H, Kosuzume H, Hayashi Y, Yamaguchi K, Suzuki Y, Itoh R., Prostaglandins Med. Mar. 1981;6(3):269-81.

Abstract of *Antithrombotic Activity and the Mechanism of Action of Trapidil (Rocornal)*, Suzuki Y, Yamaguchi K, Shimada S, Kitamura Y, Ohnishi H., Prostaglandins Leukot Med. Dec. 1982;9(6):685-95.

Abstract of *Suppression of Fibroblast Proliferation In Vitro and of Myointimal Hyperplasia In Vivo by the Triazolopyrimidine, Trapidil*, Tiell ML, Sussman II, Gordon PB, Saunders RN, Artery. 1983;12(1):33-50.

*Influence of Cardiovascular Drugs on Platelet Aggregation*, Forster W, Block HU, Giessler C, Heinroth I, Mentz P, Ponicke K, Rettkowskil W, Zehl U.,: Adv Myocardiol. 1983;4:539-47.

Abstract of *Trapidil in Preventing Restenosis After Balloon Angioplasty in the Ather Osclerotic Rabbit*, MW Liu, GS Roubin, KA Robinson, AJ Black, JA Hearn, RJ Siegel, and SB King, 3d Circulation 1990 81: 1089-1093.

Abstract of *Effects of Trapidil (Triazolopyrimidine), a Platelet-Derived Growth Factor Antagonist, in Preventing Restenosis After Percutaneous Transluminal Coronary Angioplasty*, Okamoto S, Inden M, Setsuda M, Konishi T, Nakano T, Am Heart J. Jun. 1992;123(6):1439-44.

Abstract of *Trapidil (triazolopyrimidine), A Platelet-Derived Growth Factor Antagonist, Reduces Restenosis After Percutaneous Transluminal Coronary Angioplasty. Results of the Randomized, Double-Blind STARC Study. Studio Trapidil Versus Aspirin Nella Restenosi Coronarica*, A Maresta, M Balducelli, L Cantini, A Casari, R Chioin, M Fabbri, A Fontanelli, PA Monici Preti, S Repetto, and S De Serv, Circulation, Dec. 1994; 90: 2710-2715.

Abstract of *The Trapidil Restenosis Trial (STARC study): Background, Methods and Clinical Characteristics of the Patient Population*, Maresta A, Balducelli M, Cantini L, Casari A, Chioin R, Fontanelli A, Monici Preti PA, Repetto S, Raffaghello S., Clin Trials Metaanal. Apr. 1994;29(1):31-40.

Abstract of *Fast and Reproducible Vascular Neointima Formation in the Hamster Carotid Artery: Effects of Trapidil and Captopril*, Matsuno H, Stassen JM, Hoylaerts MF, Vermylen J, Deckmyn H., Thromb Haemost. Dec. 1995;74(6):1591-6.

- *New Aspects in Antithrombotic Therapy—Platelet Inhibitors-*, Terres W, Meinertz T., Herz. Feb. 1996;21(1):1-11.

*Management of restenosis after Coronary Intervention*, Dangas G, Fuster V., Am Heart J. Aug. 1996;132(2 Pt 1):428-36.

\* cited by examiner

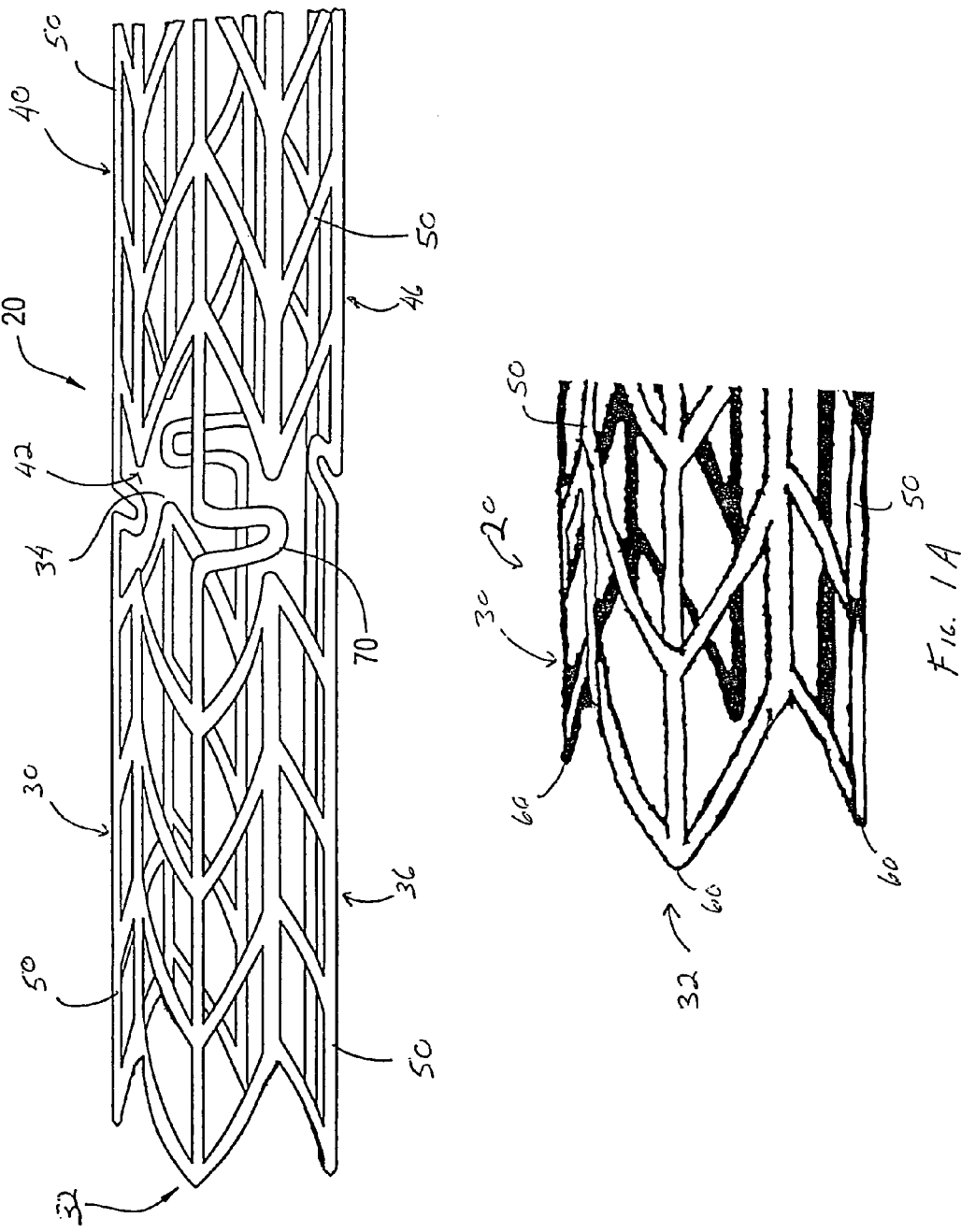

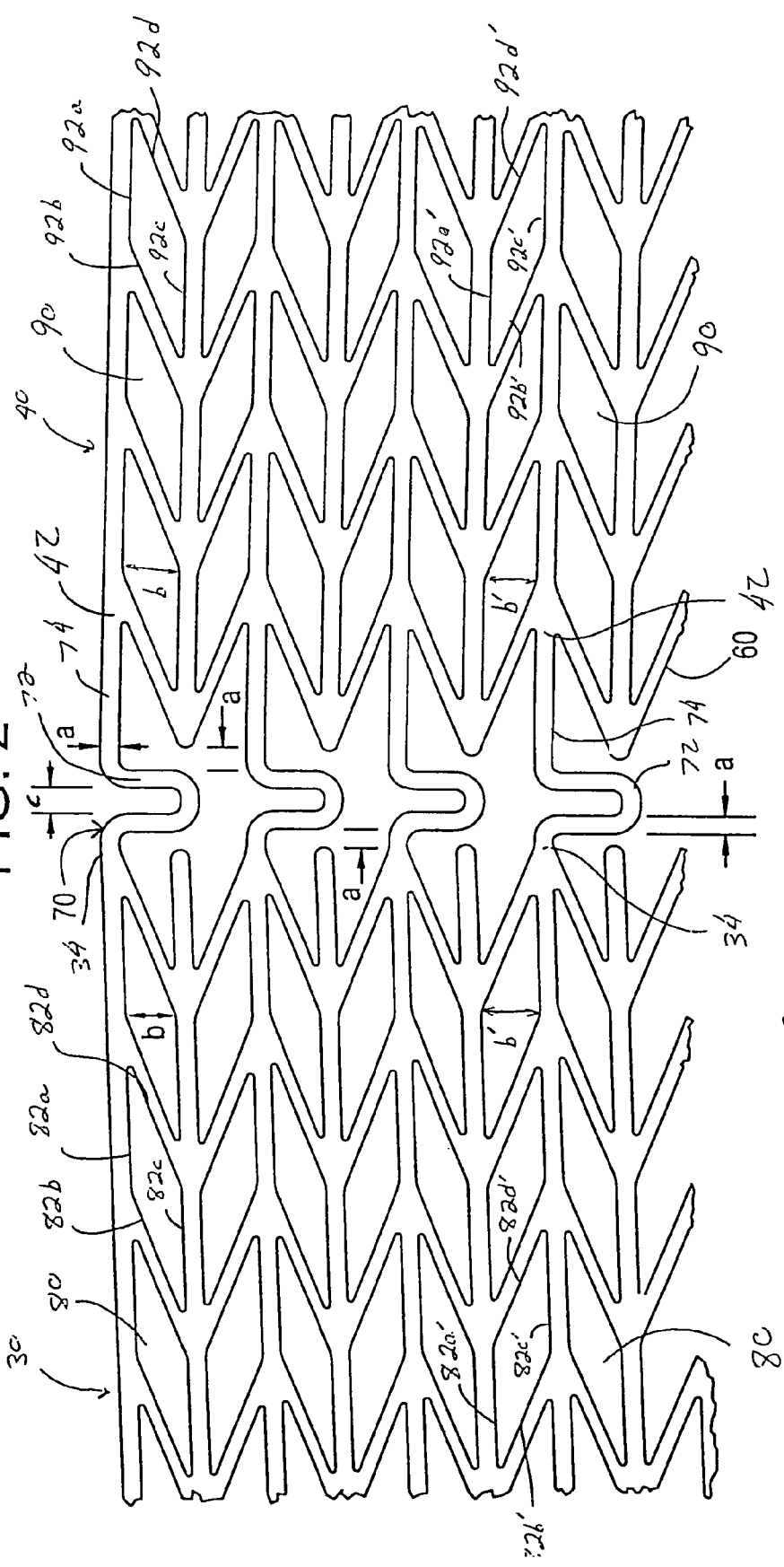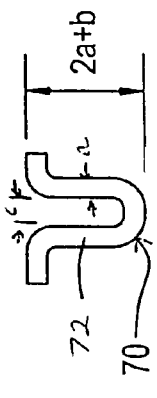

IRRADIATED STENT COATING

The present application is a continuation-in-part of co-pending U.S. patent application Ser. No. 09/771,073 filed Jan. 29, 2001 entitled "Improved Expandable Graft" which in turn is a continuation-in-part of co-pending U.S. patent application Ser. No. 09/273,736 filed Mar. 22, 1999 entitled "Improved Expandable Graft" based on U.S. Provisional Patent Application Ser. No. 60/081,824 filed Apr. 15, 1998. The present application is also a continuation-in-part of co-pending U.S. patent application Ser. No. 09/771,073 filed Jan. 29, 2001 entitled "Improved Expandable Graft" which in turn is a continuation-in-part of U.S. patent application Ser. No. 09/363,052 filed Jul. 29, 1999 (now U.S. Pat. No. 6,206,916) entitled "Coated Intraluminal Graft" based on U.S. Provisional Patent Application Ser. No. 60/094,250 filed Jul. 27, 1998.

This invention relates to an implant for use within a body and, more particularly, an expandable stent which is particularly useful for repairing various types of body cavities, and even more particularly to an expandable stent that includes and/or is at least partially coated and/or impregnated with one or more biological agents which stent and one or more biological agents are useful in repairing blood vessels narrowed or occluded by disease. Although the present invention is particularly applicable to stents, the biological agent delivery system of the present invention can be used in conjunction with various types of implants such as, but not limited to, prosthetic devices. As such, the biological agent delivery system can form one or more components of other types of implants and/or be coated and/or impregnated onto at least a portion of other types of implants to deliver one or more biological agent to a particular site. Furthermore, the biological agent delivery system can be used in conjunction with, or used separate from, a stent and/or other types of implants to deliver a biological agent into a body cavity, organ or other part of the body. In addition, the present invention is particularly directed for use in humans; however, the present invention can be used in animals and some types of plants.

INCORPORATION BY REFERENCE

U.S. Pat. Nos. 4,733,665; 4,739,762; 5,195,984; 5,725,572; 5,735,871; 5,755,781; 5,853,419; 5,861,027; 6,007,573; 6,059,810; 6,099,561; 6,200,337; and 6,206,916; U.S. patent application Ser. No. 09/273,736 filed Mar. 22, 1999; and Ser. No. 09/771,073 filed Jan. 29, 2001; and PCT Patent Application No. WO 99/56663 are incorporated herein by reference to illustrate various types and configurations of stents, the process or method of manufacturing stents, and the method by which such stents are used. U.S. Pat. Nos. 5,102,417; 5,464,650; 5,578,075; 5,616,608; 5,679,400; 5,716,981; 5,733,925; 5,981,568; and 6,206,916 and PCT Patent Application Nos. WO 90/13332; WO 91/12779; WO 99/56663; and WO 01/17577 are incorporated herein by reference to illustrate various biological agents that can be coated onto stents. These disclosed biological agents are merely a few examples of the biological agents that can be used in the present invention.

BACKGROUND OF THE INVENTION

Heart disease is still one of the most prevalent medical ailments in the world. Intraluminal endovascular grafting, a type of angioplasty procedure, has been demonstrated by experimentation to present a possible alternative to conventional vascular surgery and is used to treat heart disease. Intraluminal endovascular grafting involves a tubular prosthetic graft or stent and delivery within the vascular system. As defined herein, the terms "graft" and "stent" are used interchangeably. Advantages of this method over conventional vascular surgery include obviating the need for surgically exposing, incising, removing, replacing, or bypassing the defective blood vessel. Over 20 million angioplasty or related procedures involving occluded vasculature have been preformed worldwide. About 30% of these angioplasties fail within 30 days. These failures typically require the procedure to be repeated.

Several years ago, a product called a stent, named after Charles Stent, was introduced for use in angioplasty procedures. The stent reduced the angioplasty failure rate to about 15 percent. A stent is an expandable metal tubular device that is mounted over an angioplasty balloon and deployed at the site of coronary narrowing. The balloon is inflated to expand the stent to physically open and return patency to the body passageway. After the stent is expanded, the balloon is deflated and removed and the stent is permanently disposed to retain the opened body passageway. The first generation of expandable stents did not offer a controllable radial expansion. An improved stent disclosed in U.S. Pat. No. 4,733,665 overcame the problem associated with controlled stent expansion. However, prior art stents still do not provide control over the final, expanded configuration of the stent. For instance, the expansion of a particular coiled, spring-type stent is predetermined by the method of manufacturing, material and delivery system. In the case of self-expanding intraluminal stents, or prostheses, formed of a heat sensitive material which expands upon exposure to core body temperature, the amount of expansion is predetermined by the heat expansion properties of the particular alloy utilized in the manufacture of the intraluminal stent. Consequently, once the foregoing types of intraluminal stents were expanded at the desired location within a body passageway, the expanded size of the stent could not be increased. If the proposed expanded diameter of the narrow body passageway was not determined correctly, the stent might not expand enough to contact the interior surface of the body passageway so as to be secured thereto and/or not expand the body passageway to the desired diameter. The stent disclosed in the '665 patent overcame the problems associated with these past stent designs.

The stent based upon the '665 patent is currently being used in angioplasty procedures. Stents, including the stent of the '665 patent, are presently used in approximately 30-60 percent of all angioplasty procedures. However, these stents have several shortcomings which contribute to procedural failure rates. The currently used stents are not readily visible under fluoroscopic guidance procedures. Stent placement is hindered as a result of poor visibility. As a result, precise positioning of the stent during the insertion procedure was difficult to achieve. Consequently, the stent could be inadvertently positioned in the wrong or non-optimal location in the body passageway. These stents also shorten longitudinally after radial expansion, which is not desirable for their intended use. The shortening of the stent resulted in longitudinal movement of the stent during expansion, which sometimes resulted in the stent being fully expanded in the wrong or non-optional position. One stent design was proposed in U.S. Pat. No. 5,853,419. The stent included a hexagon in the side wall of the stent which theoretically resulted in the stent retaining its longitudinal length during expansion. The stent also included ends that flared outwardly. However, in practice, the stent does not expand as described in the '419 patent. Due to the hexagonal configuration of the openings in the stent, the struts that form the hexagonal configuration cause the ribs of the hexagonal configuration to bend, buckle or twist when the struts are being expanded, thus resulting in a reduction in the longitudinal length of the stent. The bending, buckling or twisting of the ribs can only be avoided if the struts are made of a very flexible or bendable material; however, the use of such material compromises the strength of the stent. Not only does the stent not retain its longitudinal length, the complex stent design is both difficult to manufacture and uniformly expand in a body passageway.

The improved stent disclosed in U.S. patent application Ser. No. 09/273,736 filed Mar. 22, 1999, which is incorporated herein by reference, overcomes these past problems with stents. The patent application discloses an improved stent that can be coated with one or more substances in various regions of the stent to improve the visibility of the stent by various techniques (e.g. fluoroscopy) during the insertion procedure, thereby improving the positional accuracy of the stent in the body passageway. The improved stent also incorporates a unique design which enables the stent to retain its original longitudinal length during expansion. The improved stent also is easier to manufacture and substantially uniformly expands in the body passageway.

Although the improved stent overcomes the deficiencies of prior art stents with respect to accurate stent positioning, problems can still exist with respect to tissue damage by the stent during insertion and/or expansion of the stent. The two ends of prior art stents typically include one or more rough, sharp and/or pointed surfaces. These surfaces can cause irritation and/or damage to surrounding tissue as the stent is moved within the body passageways. Such irritation or damage to the surrounding tissue can create various types of complications during the surgical procedure. These surfaces can also cause damage to surrounding tissue during the expansion of the stent. During stent expansion, the middle of the stent is first expanded by the angioplasty balloon. As the middle of the stent expands, the ends of the stent move toward one another. This movement of the ends can result in the stent ends digging into and/or penetrating the surrounding tissue. Furthermore, tissue damage can result when the end portions of the stent are eventually expanded by the angioplasty balloon. Stent designs that have flared out ends can also cause damage to tissue during insertion of the stent and expansion of the stent. U.S. patent application Ser. No. 09/771,073 filed Jan. 29, 2001, which is incorporated herein by reference, includes a stent design that overcomes or minimizes tissue damage by the stent during stent insertion and stent expansion. The stent includes rounded and/or smooth edges for the end portions of the stent.

Several problems can develop after the stent is inserted into a body passageway. One problem is known as in-stent restenosis wherein the body passageway, which has been previously treated with a stent, renarrows or closes within the stented segment. The renarrowing or closure of the body passageway can be caused by a structural failure of the stent due to contractive forces by the body passageway on the stent and/or by the body passageway growing into the openings in the stent. Other problems can include vascular narrowing and restenosis. Vascular narrowing is defined as a vascular segment that has not been previously treated by any interventional means and eventually closes, thereby preventing fluid body passageway. Restenosis is the renarrowing of a previously treated vascular segment not involving a stent. Both of these problems are the result of a body passageway that was not treated with an invasive angioplasty, narrowing or closing, and from the insertion of a stent in one portion of the body passageway causing vascular narrowing or restenosis in another part of the body passageway. Vascular narrowing, restenosis and in-stent restenosis are caused by biological factors causing the premature closing of the body passageways. One such biological factor is platelet derived growth factor, referred to as PDGF. PDGF is an intercellular messenger capable of stimulating proliferation of smooth muscle cells. Smooth muscle cells are known to migrate within body passageways such as arteries and cause a restenotic reaction.

The problems with vascular narrowing, restenosis and in-stent restenosis are significantly overcome by the use of one or more drugs. U.S. Pat. No. 6,206,916 entitled "Coated Intraluminal Graft," which is incorporated herein by reference, discloses the use of a drug coated on at least a portion of the stent to inhibit or prevent the occurrence of in-stent restenosis, vascular narrowing and/or restenosis. Although the intravenous use of drugs and/or the coating of the stent with drugs can inhibit or prevent the occurrence of in-stent restenosis, vascular narrowing and/or restenosis, the continued need for the drugs after the stent has been inserted can require the patient to be retained in the hospital for extended periods of time. Alternatively, in-stent restenosis, vascular narrowing and/or restenosis may occur days or weeks after the stent insertion procedure and after intravenous use of drugs has terminated and/or the drug coating on the stent has been dissolved off the stent. Several other United States patents disclose the use of various drugs coated on stents. For example, U.S. Pat. No. 5,716,981, which is incorporated herein by reference, discloses the use of paclitaxel or an analog or derivative thereof for use on a stent. U.S. Pat. Nos. 5,733,925 and 5,981,568, which are incorporated herein by reference, disclose the use of taxol or a water soluble taxol derivative; cytochalasin or analog thereof; or other type of cytoskeletal inhibitor for use on a stent. Several United States patents also disclose the use of polymers to bind the various drugs to the surface of the stent. Several of these polymers are disclosed in U.S. Pat. Nos. 5,578,075 and 5,679,400, which are incorporated herein by reference. U.S. Pat. No. 5,464,650, which is incorporated herein by reference, discloses the method of applying several coatings of a polymer that has been mixed with a drug so as to control the delivery of the drug in a body over a period of time. The method of coating the stent involves a series of steps that significant increases the cost, complexity and time for the manufacture of the stent.

In view of the present stent technology, there is a need and demand for a stent that has improved procedural success rates, has higher viability under fluoroscopy in vivo, retains its longitudinal dimensions from its original pre-expanded configuration to its expanded configuration, minimizes damage to tissue during insertion and expansion of the stent, inhibits or prevents the occurrence of in-stent restenosis, vascular narrowing and/or restenosis long after the stent has been inserted into a body passageway, and is simple and cost effective to manufacture.

SUMMARY OF THE INVENTION

This invention pertains to an improved expandable stent designed to meet the present day needs and demands relating to stents. The present invention is directed to a stent having a body member that includes first and second ends and a wall surface disposed between the first and second ends. The wall surface is typically formed by a plurality of intersecting elongated members, and at least some of the elongated members typically intersect with one another at a point intermediate to the first and second ends of the body member. Alternatively, or in addition, the wall surface includes one or more slots. The body member has a first cross-sectional area which permits delivery of the body member into a body passageway, and a second, expanded cross-sectional area. As defined herein, the term "body passageway" means any passageway or cavity in a living organism, including humans, animals and plants. A "body passageway" in an animal or human includes, but is not limited to, the bile duct, bronchiole tubes, blood vessels, the esophagus, trachea, ureter, urethra, the intestines, lymphatic vessels, nasal passageways, and/or the like. The invention when used in association with stents is particularly applicable for use in blood vessels, and will hereinafter be particularly described with reference thereto. The expansion of the stent body member can be accomplished in a variety of manners. Typically, the body member is expanded to its second cross-sectional area by a radially, outwardly extending force applied at least partially from the interior region of the body member. Alternatively or additionally, the body member can include heat sensitive materials that expand upon exposure to heat. The second cross-sectional area of the stent can be fixed or variable. When the second cross-sectional area is variable, the second cross-sectional area is typically dependent upon the amount of radially outward force applied to the body member. Generally, the body member is expanded so as to expand at least a portion of the body passageway while retaining the original length of the body member. In one particular body member design, the first cross-sectional shape of the body member is substantially uniformly circular so as to form a substantially tubular body member; however, the body member can have other cross-sectional shapes such as, but not limited to, elliptical, oval, polygonal, trapezoidal, and the like. As can be appreciated, the cross-sectional shape of the body member can be uniform or non-uniform in the first and/or second cross-sectional shape. In addition, if more than one body member is included in a stent, all the body members can have substantially the same size and shape, or one or more of the body members can have a different size and/or shape from one or more other body members.

Another and/or alternative feature of the present invention is that the stent includes a plurality of elongated members wherein one or more elongated members is a wire. In one embodiment, the elongated members include a plurality of wires wherein the two or more of the wires are secured to one another where a plurality of wires intersect with one another. Two or more of the wires can be connected together by a variety of techniques such as, but not limited to, welding, soldering, brazing, adhesives, lock and groove configurations, snap configurations, melting together the wires, and the like. In another embodiment, the body member is at least partially in the form of a wire mesh arrangement. The wire mesh arrangement may be utilized as the stent. The wire mesh arrangement is designed to be expanded to a second diameter within the body passageway; the second expanded diameter being variable and determined by the desired expanded internal diameter of the body passageway, whereby the expanded wire mesh arrangement will not migrate from the desired location within the body passageway, and the expansion of the stent does not cause a rupture of the body passageway. In still another embodiment, the plurality of wires forms a plurality of polygonal shaped regions on the body of the stent. In one specific design, the polygonal regions are aligned along the longitudinal axis of the body of the stent. In another specific design, the body of the stent includes a plurality of polygonal regions that are aligned along the longitudinal axis and lateral axis of the stent body. In one aspect of this specific design, the plurality of polygonal regions aligned along the longitudinal axis of the stent body are oriented substantially the same with respect to one another, and the plurality of polygonal regions aligned along the lateral axis are oriented differently from one another. In one example of this specific design, the polygonal regions that are aligned along the same longitudinal axis have a top that lies in the same longitudinal axis and have a bottom that lies in the same longitudinal axis. In addition, the polygonal regions that are aligned along the same latitudinal axis have sides that does not lie in the same latitudinal axis; however, alternating polygonal regions have sides that are substantially parallel to one another. In still another specific design, the side wall of at least one body member includes an even number of polygonal regions about the peripheral surface of the body member. In still another embodiment, the polygonal shape, upon expansion, retains the original longitudinal length of the body of the stent. In one aspect of this embodiment, a plurality of polygonal shapes have a substantially parallelogram shape. In another aspect of this embodiment, the body member includes about 2-15 polygonal shapes along the longitudinal length of the body member, typically about 2-10 polygonal shapes, and more typically about 2-8 polygonal shapes; however, more polygonal shapes can be used depending on the shape and/or size of the body member.

Yet another and/or alternative feature of the present invention is that the stent includes a plurality of elongated members wherein one or more elongated members is a thin bar. In one embodiment, the elongated members include a plurality of thin bars wherein two or more of the thin bars are secured to one another where a plurality of bars intersect with one another. Two or more of the thin bars can be connected together by a variety of techniques such as, but not limited to, welding, soldering, brazing, adhesives, lock and groove configurations, snap configurations, melting together the thin bars, and the like. In still another embodiment, the plurality of thin bars forms a plurality of polygonal shaped regions on the body of the stent. In one specific design, the polygonal regions are aligned along the longitudinal axis of the body of the stent. In another specific design, the body of the stent includes a plurality of polygonal regions that are aligned along the longitudinal axis and lateral axis of the stent body. In one aspect of this specific design, the plurality of polygonal regions aligned along the longitudinal axis of the stent body are oriented substantially the same with respect to one another, and the plurality of polygonal regions aligned along the lateral axis are oriented differently from one another. In one example of this specific design, the polygonal regions that are aligned along the same longitudinal axis have a top that lies in the same longitudinal axis and have a bottom that lies in the same longitudinal axis. In addition, the polygonal regions that are aligned along the same latitudinal axis have sides that does not lie in the same latitudinal axis; however, alternating polygonal regions have sides that are substantially parallel to one another. In still another specific design, the side wall of at least one body member includes an even number of polygonal regions about the peripheral surface of the body member. In still another embodiment, the polygonal shape, upon expansion, retains the original longitudinal length of the body of the stent. In one aspect of this embodiment, a plurality of polygonal shapes have a substantially parallelogram shape. In another aspect of this embodiment, the body member includes about 2-15 polygonal shapes along the longitudinal length of the body member, typically about 2-10 polygonal shapes, and more typically about 2-8 polygonal shapes; however, more polygonal shapes can be used depending on the shape and/or size of the body member.

Still yet another and/or alternative feature of the present invention is that the side wall of at least one body member of the stent includes a plurality of elongated members that are arranged to form at least one polygonal shape. In one embodiment, the polygonal shape, upon expansion, retains the original longitudinal length of the body of the stent. In one aspect of this embodiment, a plurality of polygonal shapes have a substantially parallelogram shape. In another aspect of this embodiment, the body member of the stent is formed from a flat piece of material. On the surface of the flat material there are formed a plurality of polygonal shaped regions. The flat material is rolled or otherwise formed and the side edges of the flat material are connected together to form the stent. The side edges of the flat material can be connected together by a variety of techniques such as, but not limited to, welding, soldering, brazing, adhesives, lock and groove configurations, snap configurations, melting together the edges, and the like. The polygonal regions in the flat material can also be formed by a variety of techniques such as, but not limited to, mechanical cutting, laser cutting, etching, molding, stamping, and/or the like. In one specific design, the polygonal regions are aligned along the longitudinal axis of the flat material. In another specific design, the flat material includes a plurality of polygonal regions are aligned along the longitudinal axis and lateral axis of the flat material. In one aspect of this specific design, the plurality of polygonal regions aligned along the longitudinal axis of the flat material are oriented substantially the same with respect to one another, and the plurality of polygonal regions aligned along the lateral axis are oriented differently from one another. In one example of this specific design, the polygonal regions that are aligned along the same longitudinal axis have a top that lies in the same longitudinal axis and have a bottom that lies in the same longitudinal axis. In addition, the polygonal regions that are aligned along the same latitudinal axis have sides that does not lie in the same latitudinal axis; however, alternating polygonal regions have sides that are substantially parallel to one another. In still another specific design, the side wall of at least one body member includes an even number of polygonal regions about the peripheral surface of the body member. In still yet another specific design, the body member includes about 2-15 polygonal shapes along the longitudinal length of the body member, typically about 2-10 polygonal shapes, and more typically about 2-8 polygonal shapes; however, more polygonal shapes can be used depending on the shape and/or size of the body member.

Another and/or alternative feature of the present invention is that the side wall of at least one body member of the stent includes at least one set of slots. In one embodiment, the one or more sets of slots are arranged to maintain the original longitudinal length of the body member when the body member is expanded. In one aspect of this embodiment, the body member of the stent is formed from a substantially flat single piece of material. On the surface of the flat material there are formed a plurality of slots. The flat material is rolled or otherwise formed and the side edges of the flat material are connected together to form the stent. The side edges of the flat material can be connected together by a variety of techniques such as, but not limited to, welding, soldering, brazing, adhesives, lock and groove configurations, snap configurations, melting together the edges, and the like. The slots in the flat material can also be formed by a variety of techniques such as, but not limited to, mechanical cutting, laser cutting, etching, molding, stamping, and/or the like. In another embodiment, at least one set of slots forms substantially a V-shape when the body member is unexpanded. In one aspect of this embodiment, body portion includes a plurality of V-shapes. In one specific design of this aspect, a plurality of V-shapes are aligned along the longitudinal axis of the side wall of the body member and are positioned in a partial stacked position with respect to one another. Generally the body member includes about 2-20 V-shapes in each set of V-shapes, typically about 2-10 V-shapes, and more typically about 2-5 V-shapes; however, more V-shapes per set can be used depending on the shape and/or size of the body member. In another specific design of this aspect, a plurality of V-shapes are aligned along the latitudinal axis of the side wall of the body member. In still another specific design of this aspect, at least a plurality of the V-shapes are substantially equally spaced from one another. In another specific design, an even number of V-shapes are aligned along the latitudinal axis of the side wall of the body member. In yet another specific design of this aspect, at least a plurality of V-shapes have substantially the same angle when the body member is unexpanded. In still yet another specific design of this aspect, the angle formed by the V-shapes is between 0-90° when the body member is unexpanded, typically about 10-75°, and more typically about 15-60°, and even more typically about 15-45°. In a further specific design of this aspect, a plurality of slots have a length dimension that is at least about twice as great as the width dimension of the slot when the body member is unexpanded, and typically at least about 3 times as great, and more typically at least about 5 times as great, and even more typically at least about 10 times as great, and still even more typically at least about 15 times as great. In still a further specific design, a plurality V-shapes in a set of V-shapes are oriented in the same direction with respect to one another and oriented such that the base of one V-shape is positioned from the base of an adjacent V-shapes a distance that is at least about 15% of the length of the legs of the V-shaped slot, typically about 15-80% of the length of the slots forming a leg of the V-shape, typically about 20-60% of the length of the leg of the V-shape, and even more typically about 30-50% of the length of the leg of the V-shape. In still yet a further specific design, a plurality of slots have a substantially oval shape. In another specific design, at least a plurality of slots that form the V-shape do not intersect with one another. In one design, none of the slots that form the V-shape intersect with one another.

Still another and/or alternative feature of the present invention is that the body member has a biocompatible coating that is coated and/or impregnated on at least a portion of its wall surface. The biocompatible coating can be used to reduce inflammation, infection, irritation and/or rejection of the stent. In one embodiment, the biocompatible coating includes, but is not limited to, a metal coating. In one aspect of this embodiment, the metal coating is plated on at least a portion of the stent. In another aspect of this embodiment, the metal coating includes, but is not limited to, gold, platinum, titanium, nickel, tin, or combinations thereof. In another embodiment, the biocompatible coating includes, but is not limited to, a polymer and/or a copolymer coating. In one aspect of this embodiment, the polymer and/or a copolymer coating includes, but is not limited to, polytetrafluoroethylene, polyethylene, poly(hydroxyethyl methacrylate) and derivatives thereof, poly(vinyl alcohol), polycaprolactone, poly(D, L-lactic acid), poly(L-lactic acid), poly(lactide-co-glycolide), poly(hydroxybutyrate), poly(hydroxybutyrate-co-valerate), polydioxanone, polyorthoester, polyanhydride, poly(glycolic acid), poly(glycolic acid-cotrimethylene carbonate), polyphosphoester, polyphosphoester urethane, poly (amino acids), cyanoacrylates, poly(trimethylene carbonate), poly(iminocarbonate), copoly(ether-esters), polyalkylene oxalates, polyphosphazenes, polyiminocarbonates, aliphatic polycarbonates, polyethylene oxide, polyethylene glycol, poly(propylene oxide), polyacrylamides, polyacrylic acid, polymethacrylic acid, poly(N-vinyl-2-pyrollidone), polyurethanes, poly(aminoacid), cellulosic polymers (e.g. sodium carboxymethyl cellulose, hydroxyethyl cellulose), collagens, carrageenan, alginate, starch, dextrin, gelatins, poly(lactide), poly(glycolide), polydioxanone, polycaprolactone, polyhydroxybutyrate, poly(phospazene), poly(phosphate ester), poly(lactide-co-glycolide), poly(glycolide-co-trimethylene carbonate), poly(glycolide-co-caprolactone), polyanhydrides, polyamides, polyesters, polyethers, polyketones, polyether elastomers, polyether amide elastomers, polyacrylate-based elastomers, polyethylene, and/or polypropylene. In still another embodiment, the biocompatible coating includes, but is not limited to, living cells.

Still yet another and/or alternative feature of the present invention is that the stent, upon expansion, substantially maintains its original longitudinal length. In one embodiment, the stent, upon expansion, substantially maintains its original longitudinal length throughout the expansion of the stent.

Another and/or alternative feature of the present invention is that the stent includes at least two body members that are connected together by at least one connector member that allows transverse bending and flexibility invariant to the plane of bending. In one embodiment, the connector member is a substantially V-shaped or U-shaped member. In another embodiment, the two body members are connected together by a plurality of connectors. In one aspect of this embodiment, two or more of the connectors are spaced at substantially equal distances from one another. In another aspect of this embodiment, two or more of the connectors are substantially symmetrically oriented from one another. In still another aspect of this embodiment, at least three connectors connect together two body members, and typically about 3-20 connectors connect together two body members, and even more typically about 3-10 connectors connect together two body members. In still another embodiment, the size of the connector is limited so as not to interfere with the proper expansion of the stent. In one aspect of this embodiment, the substantially V-shaped or U-shaped member has a height that is less than about five times the maximum height of a polygonal shape in the unexpanded stent, and typically less than about three times the maximum height of a polygonal shape in the unexpanded stent, and more typically less than about two times the maximum height of a polygonal shape in the unexpanded stent, and even more typically less than about 1.75 times the maximum height of a polygonal shape in the unexpanded stent, and yet even more typically less than about 1.5 times the maximum height of a polygonal shape in the unexpanded stent, and still yet even more typically less than about 1.3 times the maximum height of a polygonal shape in the unexpanded stent. In another aspect of this embodiment, the substantially V-shaped or U-shaped member has a height that is less than about 1.5 times the maximum width of the V-shape in the unexpanded stent, and typically less than about 1.0 times the maximum width of the V-shape in the unexpanded stent, and more typically less than about 0.75 times the maximum width of the V-shape in the unexpanded stent, and even more typically less than about 0.65 times the maximum width of the V-shape in the unexpanded stent, and yet typically less than about 0.5 times the maximum width of the V-shape in the unexpanded stent, and still yet more typically less than about 0.4 times the maximum width of the V-shape in the unexpanded stent.

Yet another and/or alternative feature of the present invention is that the body member is made of and/or includes a material that is visible under fluoroscopy in vivo. The material to increase visibility includes, but is not limited to, metals, polymers and/or copolymers. In one embodiment, the material to increase visibility is adhered to the surface of at least a portion of the stent by coating, plating, mounting, welding and/or braising. In another embodiment, the material to increase visibility is secured to the stent so as to principally come in contact with the inner luminal surface of the body passageway. For instance, when the stent is inserted into a vessel, the material to increase visibility primarily contacts the inner luminal surface of the vessel and not any blood-borne components that could accelerate stent failure rates. In one aspect of this embodiment, the material to increase visibility is at least partially located at least one end, and typically both ends, of the body member. This positioning of the material on the body member helps to identify the location of the ends of the body member and the stent as a whole, thus enhancing the critical placement of the stent so as to reduce the failure rate. In another aspect of this embodiment, the material to increase visibility is at least partially located on the outer surface of the body member at the connector member of the stent. This location of the material also enhances the critical placement of the stent around areas of high tortuosity so as to reduce the failure rate. In still another embodiment, the material to increase visibility includes gold. In one aspect of this embodiment, the gold is plated on at least a portion of the stent.

Still another and/or alternative feature of the present invention is that the stent material is treated with gamma, beta and/or e-beam radiation to reduce the vascular narrowing of the stented section. The radiation treatment can inactivate the cell migration and properties thereof within a 3 mm depth of the arterial wall. The radiation treatment further sterilizes the stent to reduce infection when the stent is inserted into a body passageway.

Another and/or alternative feature of the present invention is that the stent can be inserted and expanded by standard procedures. Therefore, the stent can be inserted into a body passageway until it is disposed at the desired location within the body passageway. The stent can then be radially expanded outwardly into contact with the body passageway until the body passageway, at the desired location, has been expanded, whereby the stent inhibits or prevents the body passageway from collapsing. In one embodiment, the stent is at least partially expanded by an angioplasty balloon.

Still another and/or alternative feature of the present invention is a stent that includes rounded, smooth and/or blunt surfaces that minimize and/or prevent damage to body cavities as the stent is inserted into a body passageway and/or expanded in a body passageway. The modified end surfaces are designed to reduce the cutting and/or piercing of tissue as the stent is positioned in and/or expanded in a body passageway. Typically, the path from the point of entry into a body passageway, and the final position of the stent in the body passageway, are not straight. As a result, the stent is caused to be weaved through the body passageway to reach the final position in the body passageway. This weaving of the stent can result in the front ends, back ends, and/or side walls of the stent to cut, scrape or otherwise damage tissue in the body passageway as the stent is moved in the body passageway. The rounding, smoothing and/or blunting of the surfaces significantly reduces possible damage to the tissue. Damage to the tissue in the body passageway can also occur during the expansion of the stent. The rounding, smoothing and/or blunting of the surfaces likewise significantly reduces possible damage to the tissue during the expansion of the stent. In one embodiment, the rounding, smoothing and/or blunting of the surfaces can be accomplished by a number of different procedures. Some of these procedures include, but are not limited to, buffing, grinding, and/or sanding the surfaces. In another embodiment, the surfaces of the stent are smoothed by coating and/or impregnating the stent with one or more metals or compounds. In one aspect of this embodiment, at least a portion of the stent is coated and/or impregnated with a polymer and/or copolymer so as to reduce or eliminate the sharp, rough, and/or pointed surfaces on the stent.

A further and/or alternative feature of the present invention is that the stent is at least partially coated and/or impregnated with one or more vascular active agents that inhibit and/or reduce restenosis, vascular narrowing and/or in-stent restenosis. In one embodiment, at least one of the vascular active agents affects or alters tissue contraction and/or expansion to inhibit and/or reduce restenosis, vascular narrowing and/or in-stent restenosis. Prior substances have been coated onto stents to address one or more problems associated with the use of stents. These substances include aspirin, heparin, colchicine and dexamethazone, among others. These substances are used to inactivate platelets, stop cell division and prevent cell adhesion. The problems associated with the use of these substances have varied effects. Heparin is not potent enough to extend a clinical effect. Colchicine has been shown to kill the cells in the surrounding area and actually propagate the problem. Dexamethazone has not provided the desired restenosis prevention. As defined herein, the term "vascular active agent" is defined as a substance other than aspirin, colchicine, dexamethazone, or heparin. The vascular active agent is formulated to inhibit, reduce, and/or prevent restenosis, vascular narrowing and/or in-stent restenosis in a body passageway. As can be appreciated, the vascular active agent can be used independently of or in combination with a "secondary vascular active agent." In one embodiment, the secondary vascular active agent includes, but is not limited to, an agent that inhibits, reduces, and/or prevents thrombosis. Such agent can include, but is not limited to, antithrombotic compounds, anti-platelet compounds, and/or anticoagulant compounds. In addition, the "secondary vascular active agent" can include compounds that include, but are not limited to, metabolic inhibitors, antineoplastics, proliferation inhibitors, cytotoxic compounds, antiplatelets, anti-coagulants, fribrinolytics, thrombin inhibitors, antimitotics, anti-inflammatory compounds, radioactive isotopes, and/or anti-tumor compounds. Furthermore, the "secondary vascular active agent" can include, but is not limited to, DNA, plasmid DNA, RNA, plasmid RNA, ACE inhibitors, growth factors, cholesterol-lowering agents, vasodilating agents, oligonucleotides, and/or anti-sense oligonucleotides. Specific secondary vascular active agents that can be used include, but are not limited to, aspirin, colchicine, heparin, glucocorticoids (e.g. dexamethazone, betamethazone), hirudin, tocopherol, angiopeptin, D-Phe-ProArg chloromethyl ketone, and/or derivatives of these compounds. Heretofore, Applicant is unaware of stents being coated and/or impregnated with a combination of at least one vascular active agent and at least one secondary vascular active agent. In addition, Applicant is unaware of stents being coated and/or impregnated with a combination of two or more secondary vascular active agents. Although the prior use of a single secondary vascular active agent has not resolved problems associated with in-stent restenosis, vascular narrowing and/or restenosis, the combination of two or more of these compounds coated and/or impregnated on the stent can provide better results. The scope of this invention encompasses the concept of at least partially coating and/or impregnating the stent with two or more secondary vascular active agents by themselves or in combination with one or more vascular active agents. In one aspect of this embodiment, the vascular active agent includes a compound that at least partially inhibits PDGF activity in the body passageway. After a stent is inserted into a body passageway, the stent may induce some irritation in the body passageway. The biological factor, PDGF, is turned on due to such irritation and activates the components of clotting. These components can cause clotting in the stent area or in adjacent areas. This clotting can cause the body passageway to narrow or ultimately close. At least one or more substances coated and/or impregnated onto the stent are formulated to deactivate and/or inhibit the activity of the PDGF, thereby reducing the occurrence of in-stent restenosis, vascular narrowing and/or restenosis. In another aspect of this embodiment, at least one of the vascular active agents that is at least partially coated and/or impregnated onto the stent to inhibit PDGF activity in the body passageway includes triazolopyrimidine (Trapidil). When the stent is inserted into a body passageway, some damage to the tissue of the body passageway can occur. For instance, a damaged endothelium exposes the connective tissue to platelet aggregation and to local release of PDGF. Numerous animal models have shown that platelet adhesion to the vascular wall of this damaged endothelium soon triggers the proliferation and migration of smooth muscle cells. If platelets are a source of PDGF, it has now been demonstrated that endothelial cells, macrophages and smooth muscle cells are also a source of PDGF following vascular trauma. The influence of Trapidil on platelet aggregation is linked to inhibition of the synthesis of thromboxane A2 and the partial blocking of thromboxane A2 receptors. Trapidil is able to normalize an incorrect balance between thromboxane A2 and prostacycline. Thromboxane A2 is a powerful inducer of platelet aggregation. Thromboxane A2 is also responsible for the contraction of smooth muscles or vessels and stimulates the proliferation of the arterial intimal cells. Prostacyclin inhibits platelet aggregation and has vasodilator properties. Trapidil also has antithrombotic properties and can significantly reduce thrombosis induced by creation of an arteriovenous conduit, as compared to aspirin and dipyridamoles, which only had a modest effect. Trapidil has other desirable properties such as vasodilation, a decrease in angina and an increase in HDL levels in patients with ischemic heart disease. Trapidil effectively inhibits of restenosis. Trapidil has an affinity to exert clinical effects starting in the second hour of treatment. The platelet inhibition in the first day of treatment with Trapidil continues through the thirtieth day. The philosophy of a multifactorial approach, including but not limited to the increasing success of angioplasty and stent associated with a considerable reduction in complications, promotes the use of this technique in a large scale in the treatment of patients with coronary heart disease. Restenosis is one of the most important limitations to the long term benefits of angioplasty and a stent combination. A pharmacological approach aiming to intervene in the mechanism of restenosis is needed to supplement the mechanical approach of the revascularization procedure. Various approaches have been proposed for the prevention of restenosis. The use of drugs such as, but not limited to, Trapidil, delivered by a stent locally to the affected area satisfies this need. As can be appreciated, Trapidil can be used in combination with one or more other vascular active agents and/or in combination with one or more secondary vascular active agents. The amount of Trapidil coated and/or impregnated into the stent can be varied depending on the intended use of the stent and/or size of the stent. In one embodiment, the stent includes up to about 200 mg of Trapidil. In one aspect of this embodiment, the stent includes at least about 1 μg of Trapidil. In another aspect of this embodiment, the stent includes about 10 μg to about 50 mg of Trapidil. In still another aspect of this embodiment, the stent includes about 20 μg to about 10 mg of Trapidil.

Still a further and/or alternative feature of the present invention is that the stent is at least partially coated and/or impregnated with one or more vascular active agents that promote blood vessel growth. The fully or partially blocked blood vessel and tissue about the fully or partially blocked blood vessel become oxygen starved due to the impaired flow of blood through the fully or partially blocked blood vessels. When a stent in inserted into the blood vessel to reestablish a more normal blood flow rate through the blood vessel, the region around the formerly fully or partially blocked blood vessel once again begins to receive a proper oxygen supply. However, prolonged oxygen starvation can damage the blood vessels and surrounding tissue to an extent that a substantial time period is required to naturally repair such damaged tissue. Furthermore, the formerly blocked or partially blocked blood vessel may be weaker resulting in further damage to the blood vessel once normal blood flow rates are reestablished. Many of these problems can be addressed by at least partially coating and/or impregnating the stent with one or more vascular active agents that promote blood vessel growth. One non-limiting blood vessel growth promoter that can be coated and/or impregnated on the stent is granulo-cyte-macrophage colony-stimulating-factor (GM-CSF). GM-CSF has been found to simulate blood vessel growth even in oxygen starved environments. As can be appreciated, GM-CSF can be used in combination with one or more other vascular active agents and/or in combination with one or more secondary vascular active agents. The amount of GM-CSF coated and/or impregnated into the stent can be varied depending on the intended use of the stent and/or size of the stent. In one embodiment, the stent includes up to about 200 mg of GM-CSF. In one aspect of this embodiment, the stent includes at least about 1 µg of GM-CSF. In another aspect of this embodiment, the stent includes about 10 µg to about 50 mg of GM-CSF. In still another aspect of this embodiment, the stent includes about 20 µg to about 10 mg of GM-CSF.

Yet another and/or alternative feature of this invention corresponds to the local delivery of the vascular active agent to inhibit and/or prevent restenosis, vascular narrowing and/or in-stent restenosis including, but not limited to, Trapidil, through an angioplasty balloon with the physical capability to transfer solute of the vascular active agent through the angioplasty balloon membrane to the affected sight. As can be appreciated, a secondary vascular active agent such as, but not limited to, GM-CSF, can be delivered in combination with the vascular active agent or in alternative to the vascular active agent. This delivery can be in the form of a stream, a slow oozing delivery or a bolus injection. The delivery can be made through magnetic, electrical or physical arrangements. In one embodiment, the delivery of a vascular active agent and/or secondary vascular active agent is accomplished through a separate passageway capable of channeling the solute of the vascular active agent to the affected area. This delivery through an angioplasty balloon also delivers the vascular active agent and/or secondary vascular active agent to the sight of restenosis, vascular narrowing, in-stent restenosis, thrombosis and the like, and/or the site to promote growth of blood vessels. In one aspect of this embodiment, the angioplasty balloon includes one or more slits or openings wherein the vascular active agent and/or secondary vascular active agent can stream, ooze or otherwise flow out of the angioplasty balloon and into the body passageway. The one or more slits and/or openings can be designed so as to allow the vascular active agent and/or secondary vascular active agent to exit the angioplasty balloon when the angioplasty balloon is in an expanded and unexpanded state. In one specific design, the one or more slits and/or openings in the angioplasty balloon inhibit or prevent the vascular active agent and/or secondary vascular active agent from entering the body passageway when the angioplasty balloon is in the unexpanded state.

Another and/or alternative feature of the present invention is that the vascular active agent can inhibit and/or reduce restenosis, vascular narrowing and/or in-stent restenosis, and/or can promote blood vessel growth, and/or secondary vascular active agent is at least partially coated and/or impregnated on specific regions of the stent or totally coats the stent. The thickness of the coating on the stent can be uniform or varied. Generally, the thickness of the coating is not as important as the concentration of the vascular active agent and/or secondary vascular active agent needed to acquire the desired affect. High concentrations of vascular active agents and/or secondary vascular active agents can be coated with thinner coatings, and lower concentrations of vascular active agents and/or secondary vascular active agents can be coated with thicker coatings.

Still another and/or alternative feature of the present invention is that the vascular active agent can inhibit and/or reduce restenosis, vascular narrowing and/or in-stent restenosis, and/or can promote blood vessel growth, and/or secondary vascular active agent is at least partially coated and/or impregnated onto the stent by the use of an intermediate compound. Typically, the compound is a synthetic biocompatible material that does not adversely affect the vascular active agent and/or secondary vascular active agent or cause problems or adverse reactions in the body passageway.

Still yet another and/or alternative feature of the present invention is that the stent and/or implant such as, but not limited to, a prosthetic device, is at least partially coated and/or impregnated with, and/or at least partially includes one or more biological agents. As defined herein, the term "biological agent" is defined as any substance, drug or otherwise, that is formulated or designed to prevent, inhibit and/or treat one or more biological problems, such as, but not limited to, viral, fungus and/or bacteria infection; vascular disorders; digestive disorders; reproductive disorders; lymphatic disorders; cancer; implant rejection; pain; nausea; swelling; arthritis; bone disease; organ failure; immunity diseases; cholesterol problems; blood diseases; lung diseases and/or disorders; heart diseases and/or disorders; brain diseases and/or disorders; neuroglial diseases and/or disorders; kidney diseases and/or disorders; ulcers; liver diseases and/or disorders; intestinal diseases and/or disorders; gallbladder diseases and/or disorders; pancreatic diseases and/or disorders; psychological disorders; respiratory disorders; gland disorders; skin diseases; hearing disorders; oral disorders; nasal disorders; eye disorders; fatigue; genetic disorders; burns; scars; trauma; weight disorders; addiction disorders; hair loss; cramps; muscle spasms; tissue repair; and/or the like. As such, the term "biological agent" includes vascular active agents and secondary vascular active agents. In one embodiment, the "biological agent" includes the "vascular active agents" and "secondary vascular active agents" discussed above.

A further another and/or alternative feature of the present invention is that the biological agent is at least partially encapsulated by a material. In one embodiment, the biological agent includes one or more vascular active agents and/or one or more secondary vascular active agents to inhibit and/or reduce restenosis, vascular narrowing and/or in-stent restenosis. In another embodiment, the biological agent is at least partially encapsulated in biodegradable polymer and/or copolymer. In one aspect of this embodiment, the polymer and/or copolymer is at least partially formulated from aliphatic polyester compounds such as, but not limited to, PLA (i.e. poly(D, L-lactic acid), poly(L-lactic acid)) and/or PLGA (i.e. poly(lactide-co-glycoside)). In still another embodiment, the rate of degradation of the polymer and/or copolymer is principally a function of 1) the water permeability and solubility of the polymer and/or copolymer, 2) chemical composition of the polymer and/or copolymer, 3) mechanism of hydrolysis of the polymer and/or copolymer, 4) the biological agent encapsulated in the polymer and/or copolymer, 5) the size, shape and surface volume of the polymer and/or copolymer, 6) porosity of the polymer and/or copolymer, and/or 7) the molecular weight of the polymer and/or copolymer. As can be appreciated, other factors may also affect the rate of degradation of the polymer and/or copolymer. The rate of degradation of the polymer and/or copolymer controls the amount of biological agent released during a specific time period into the body passageway or other parts of the body. As can be appreciated, the biological agent can be formed into a pill, capsule or the like for oral ingestion by a human or animal. The rate of degradation of the polymer and/or copolymer that is at least partially encapsulating the biological agent controls the amount of biological agent that is released into a body passageway or other part of the body over time. The biological agent can be at least partially encapsulated with different polymer and/or copolymer coating thickness, different numbers of coating layers, and/or with different polymers or copolymers to alter the time period one at least partially encapsulated biological agent is released in a body passageway or other part of the body over time as compared to another at least partially encapsulated biological agent. Alternatively or in addition, one or more at least partially encapsulated biological agents can be at least partially encapsulated in a biodegradable capsule and/or coating, which biodegradable capsule and/or coating delays the exposure of one or more of the at least partially encapsulated biological agents to fluids in a body passageway or other part of the body. As can further be appreciated, the at least partially encapsulated biological agent can be introduced into a human or animal by means other than by oral introduction, such as, but not limited to, injection, topical applications, intravenously, eye drops, nasal spray, surgical insertion, suppositories, intrarticularly, intraocularly, intranasally, intradermally, sublingually, intravesically, intrathecally, intraperitoneally, intracranially, intramuscularly, subcutaneously, directly at a particular site, and the like. In another aspect of this embodiment, the polymer and/or copolymer is formed into one or more shapes such as, but not limited to, spherical, cubical, cylindrical, pyramidal, and the like.

Yet a further another and/or alternative feature of the present invention is that the stent and/or implant is at least partially coated and/or impregnated with one or more polymers or copolymers that include one or more biological agents. In one embodiment, at least one biological agent is combined with a coating compound and at least partially coated and/or impregnated on the stent or other implant. In one aspect of this embodiment, at least one biological agent is mixed with the coating compound prior to the coating compound being at least partially applied to the stent or other implant. In another aspect of this embodiment, at least one biological agent is first applied to at least a portion of the stent or other implant and the coating compound is applied over at least a portion of the one or more biological agents. In still another aspect of this embodiment, the coating compound is first applied to at least a portion of the stent or other implant and at least one biological agent is at least partially coated onto the coating compound. As can be appreciated, the stent or other implant can be at least partially impregnated and/or coated with one or coating layers of biological agent, coating compound, coating compound plus biological agent. Furthermore, the coating compositions and/or thicknesses can be the same or different. In addition, the concentration and/or type of biological agents in each coating that is coated onto the stent or implant can be the same or different. Still further, the coating thickness and/or coating composition for each coating layer in various regions of the stent or other implant can be the same or different. Generally, the coating thickness of each coating on the stent or other implant is less than about 0.08 inch, and typically less than about 0.01 inch, and even more typically less than about 0.005 inch. The particular coating sequence on a stent or other implant will generally depend on 1) the amount of a particular biological agent to be released over time, 2) the sequence of biological agents to be released over time, 3) the time period the release of the biological agent is to begin, 4) the time period the release of the biological agent is to end, and/or 5) the location in the body the biological agent is to be released. As can be appreciated, other factors may dictate the particular coating sequence on a stent or other implant. The coating compound is formulated to delay and/or regulate the time and/or amount of one or more biological agents being released into the body passageway or other part of the body; and/or to facilitate in the bonding of one or more biological agents to the stent or other implant. The coating compound can be a biodegradable compound, a non-biodegradable compound, or a partially biodegradable compound. The coating compound can be formulated so as to form one or more bonds with one or more biological agents or be chemically inert with respect to one or more biological agents.

Still a further another and/or alternative feature of the present invention is that the stent and/or implant is at least partially formed by a material that includes one or more biological agents. In one embodiment, one or more biological agents are at least partially embedded in the stent or other implant so as to prevent the release, control the release, and/or delay the release of one or more biological agents into the body passageway or other part of the body. The material forming at least a portion of the stent or other implant in which one or more biological agents are imbedded can be a biodegradable material, a non-biodegradable material, or a partially biodegradable material. The material can be formulated so as to form one or more bonds with one or more biological agents or be chemically inert with respect to one or more biological agents. Typically, the material is a substantially non-biodegradable material so that the structural integrity of the stent or other implant is maintained throughout the life of the stent or other implant. However, there may be instances wherein the stent or other implant advantageously becomes fully or partially degraded over time, thus in such instances, the material can be biodegradable or partially biodegradable. In one aspect of this embodiment, the material includes a metal and/or polymer and/or copolymer. In another embodiment, the material is at least partially coated and/or impregnated with one or more coating materials. The coating material can be biodegradable, non-biodegradable, or partially biodegradable. The coating can include one or more biological agents. In one aspect of this embodiment, the coating material at least partially delays and/or controls the release of one or more biological agents from the material that at least partially forms the stent or other implant. In another aspect of this embodiment, the coating material includes one or more biological agents that are at least partially released from the coating material together with or exclusive from the one or more biological agents in the material of the stent or other implant.

Still a further another and/or alternative feature of the present invention is that one or more biological agents at least partially forms a chemical bond with a material that at least partially encapsulates one or more of the biological agents; that at least partially coats and/or impregnates the stent or other implant; and/or that at least partially forms the stent or other implant. In one embodiment, one or more of the biological agents forms a polymer and/or copolymer salt complex with a material that at least partially encapsulates one or more of the biological agents; that at least partially coats and/or impregnates the stent or other implant; and/or that at least partially forms the stent or other implant. In one aspect of this embodiment, the biological agent includes, but is not limited to, Trapidal and/or derivatives thereof; GM-CSF and/or derivatives thereof; taxol and/or derivatives thereof (e.g. taxotere, baccatin, 10-deacetyltaxol, 7-xylosyl-10-deacetyltaxol, cephalomannine, 10-deacetyl-7-epitaxol, 7 epitaxol, 10-deacetylbaccatin III, 10-deacetylcephaolmannine); 5-Fluorouracil and/or derivatives thereof; Beta-Estradiol and/or derivatives thereof; Tranilast and/or derivatives thereof; Probucol and/or derivatives thereof; Angiopeptin and/or derivatives thereof; paclitaxel and/or derivatives thereof; cytochalasin and/or derivatives thereof (e.g. cytochalasin A, cytochalasin B, cytochalasin C, cytochalasin D, cytochalasin E, cytochalasin F, cytochalasin G, cytochalasin H, cytochalasin J, cytochalasin K, cytochalasin L, cytochalasin M, cytochalasin N, cytochalasin O, cytochalasin P, cytochalasin Q, cytochalasin R, cytochalasin S, chaetoglobosin A, chaetoglobosin B, chaetoglobosin C, chaetoglobosin D, chaetoglobosin E, chaetoglobosin F, chaetoglobosin G, chaetoglobosin J, chaetoglobosin K, deoxaphomin, proxiphomin, protophomin, zygosporin D, zygosporin E, zygosporin F, zygosporin G, aspochalasin B, aspochalasin C, aspochalasin D); aspirin and/or derivatives thereof; dipyridamoles and/or derivatives thereof; argatroban and/or derivatives thereof; forskolin and/or derivatives thereof; vapiprost and/or derivatives thereof; prostacyclin and prostacyclin and/or derivatives thereof; glycoprotein IIb/IIIa platelet membrane receptor antibody; colchicine and/or derivatives thereof; dexamethazone and/or derivatives thereof; dipyridamoles and/or derivatives thereof; and/or heparin and/or derivatives thereof; glucocorticoids (e.g. dexamethasone, betamethasone) and/or derivatives thereof; hirudin and/or derivatives thereof; coumadin and/or derivatives thereof; prostacyclenes and/or derivatives thereof; antithrombogenic agents; steroids; seramin and/or derivatives thereof, thioprotese inhibitors; nitric oxide; ibuprofen; antimicrobials; antibiotics; tissue plasma activators; rifamycin and/or derivatives thereof; monoclonal antibodies; antifibrosis compounds; cyclosporine; hyaluronate; protamine and/or derivatives thereof; tocopherol and/or derivatives thereof; angiopeptin and/or derivatives thereof; tick anticoagulant protein and/or derivatives thereof; methotrexate and/or derivatives thereof; azathioprine and/or derivatives thereof; vincristine and/or derivatives thereof; vinblastine and/or derivatives thereof; fluorouracil and/or derivatives thereof; adriamycin and/or derivatives thereof; mutamycin and/or derivatives thereof; Anti-Invasive Factor; Cartilage-Derived Inhibitor; retinoic acids and/or derivatives thereof, Suramin; Tissue Inhibitor of Metalloproteinase-1 and/or derivatives thereof; Tissue Inhibitor of Metalloproteinase-2 and/or derivatives thereof; Plasminogen Activator Inhibitor-1 and/or derivatives thereof; Plasminogen Activator Inhibitor-2 and/or derivatives thereof; estramustine and/or derivatives thereof; methotrexate and/or derivatives thereof, curacin-A and/or derivatives thereof; epothilone and/or derivatives thereof; vinblastine and/or derivatives thereof; tBCEV and/or derivatives thereof; lighter "d group" transition metals (e.g ammonium metavanadate, sodium metavanadate, sodium orthovanadate, vanadyl acetylacetonate, vanadyl sulfate mono- and trihydrates, ammonium tungstate, calcium tungstate, sodium tungstate dihydrate, tungstic acid, tungsten (IV) oxide, tungsten (VI) oxide, ammonium molybdate and its hydrates, sodium molybdate and its hydrates, potassium molybdate and its hydrates, molybdenum (VI) oxide, molybdenum (VI) oxide, molybdic acid, molybdenyl acetylacetonate); Platelet Factor 4; growth factors (e.g. VEGF; TGF; IGF; PDGF; FGF); Protamine Sulphate (Clupeine); Sulphated Chitin Derivatives; Sulphated Polysaccharide Peptidoglycan Complex; Staurosporine; proline analogs (L-azetidine-2-carboxylic acid (LACA); cishydroxyproline; d,L-3,4-dehydroproline; Thiaproline; alpha-dipyridyl; beta aminopropionitrile fumarate; 4-propyl-5-(4-pyridinyl)-2 (3H)-oxazolone; Methotrexate Mitoxantrone; Interferons; alpha 2 Macroglobulin; ChIMP-3; Chymostatin; beta-Cyclodextrin Tetradecasulfate; Eponemycin; Camptothecin; Fumagillin; Gold Sodium Thiomalate; D-Penicillamine; beta-1-anticollagenase; alpha 2-antiplasmin; Bisantrene; Lobenzarit disodium (N-(2)-carboxyphenyl-4-chloroanthronilic acid disodium; Thalidomide; Angiostatic steroid; AGM-1470; carboxynaminolmidazole; penicillins; cephalosporins (e.g. cefadroxil, cefazolin, cefaclor); aminoglycosides (e.g. gentamycin, tobramycin; sulfonamides (e.g. sulfamethoxazole); rapamycin, metronidazole; prednisone; prednisolone; hydrocortisone; adrenocorticotropic hormone; sulfasalazine; naproxen; fenoprofen; indomethacin; phenylbutazone; acyclovir; ganciclovir; zidovudine; nystatin; ketoconazole; griseofulvin; flucytosine; miconazole; clotrimazole; pentamidine isethionate; quinine; chloroquine; mefloquine; thyroid hormone; estrogen; progesterone; cortisone; growth hormone; insulin; $T_H 1$ (e.g., Interleukins-2, -12, and -15, gamma interferon); $T_H 2$ (e.g. Interleukins-4 and -10) cytokines); estramustine; epothilone; curacin-A; colchicine; methotrexate; vinblastine; 4-tert-butyl->3-(2-chloroethyl) ureido!benzene ("tBCEU"); alpha-adrenergic blocking agents; angiotensin II receptor antagonists; receptor antagonists for histamine; serotonin; serotonin blockers; endothelin; inhibitors of the sodium/hydrogen antiporter (e.g., amiloride and derivatives thereof); agents that modulate intracellular $Ca^{2+}$ transport such as L-type (e.g., diltiazem, nifedipine, verapamil) or T-type $Ca^{2+}$ channel blockers (e.g. amiloride); calmodulin antagonists (e.g., $H_7$); inhibitors of the sodium/calcium antiporter (e.g. amiloride); ap-1 inhibitors (for tyrosine kinases, protein kinase C, myosin light chain kinase, $Ca^{2+}$/calmodulin kinase II, casein kinase II); anti-depressants (e.g. amytriptyline, fluoxetine, LUVOX® and PAXIL®); cytokine and/or growth factors as well as their respective receptors, (e.g., the interleukins, alpha, beta or gamma-IFN (interferons), GM-CSF, G-CSF, epidermal growth factor, transforming growth factors alpha and beta, TNF, and antagonists of vascular epithelial growth factor, endothelial growth factor, acidic or basic fibroblast growth factors, and platelet derived growth factor); inhibitors of the $IP_3$ receptor; protease; collagenase inhibitors; nitrovasodilators (e.g. isosorbide dinitrate); anti-mitotic agents (e.g. colchicine, anthracyclines and other antibiotics, folate antagonists and other anti-metabolites, vinca alkaloids, nitrosoureas, DNA alkylating agents, topoisomerase inhibitors, purine antagonists and analogs, pyrimidine antagonists and analogs, alkyl sulfonates); immunosuppressive agents (e.g. adrenocorticosteroids, cyclosporine); sense or antisense oligonucleotides (e.g. DNA, RNA, plasmid DNA, plasmid RNA, nucleic acid analogues (e.g. peptide nucleic acids); inhibitors of transcription factor activity (e.g. lighter d group transition metals); anti-neoplastic compounds; chemotherapeutic compounds (e.g. 5-fluorouracil, vincristine, vinblastine, cisplatin, doxyrubicin, adriamycin, or tamocifen), radioactive agents (e.g. Cu-64, Ca-67, Cs-131, Ga-68, Zr-89, Ku-97, Tc-99m, Rh-105, Pd-103, Pd-109, In-111, I-123, I-125, I-131, Re-186, Re-188, Au-198, Au-199, Pb-203, At-211, Pb-212, Bi-212, $H_3P^{32}O_4$); 7E-3B; CAPTOPRIL; CILAZAPRIL; LISINOPRIL; LOVASTATIN; nitroprusside; phosphodiesterase inhibitors; prostaglandin inhibitors; thioprotease inhibitors; triazolopyrimidine and/or derivatives thereof; calcium channel blockers; toxins (e.g. ricin, abrin, diphtheria toxin, cholera toxin, gelonin, pokeweed antiviral protein, tritin, Shigella toxin, and Pseudomonas exotoxin A); metalloproteinase inhibitors; ACE inhibitors; growth factors; oligonucleotides; antiplatelet compounds; antitabolite compounds; anti-inflammatory compounds; anticoagulent compounds; antimitotic compounds; antioxidants; antimetabolite compounds (e.g staurosporin, trichothecenes, and modified diphtheria and ricin toxins, Pseudomonas exotoxin); antimigratory agents (e.g. caffeic acid derivatives, nilvadipine); anti-matrix compounds (e.g. colchicine, tamoxifen); protein kinase inhibitors (e.g staurosporin); anti-vital compounds, anti-fungal compounds and/or anti-protozoal compounds. As can be appreciated, the biological agent can include other compounds. In one specific example of this aspect, the Trapidil forms a salt complex with the coating compound such that the Trapidil forms the cation component and the coating compound forms the anionic component.

Still another and/or alternative feature of the present invention, the material used to at least partially encapsulate one or more biological agents; at least partially coat and/or impregnate the stent or other implant; and/or at least partially form the stent or other implant is a polymer and/or copolymer. In one embodiment, the polymer and/or copolymer includes one or more carboxylate groups, phosphate groups, sulfate groups, and/or other organic anion groups. In one aspect of this embodiment, the polymer and/or copolymer includes one or more groups which form one or more anionic bonding sites for cationic salts of the biological agent. In one aspect of this embodiment, the polymer and/or copolymer includes one or more groups that form one or more cationic bonding sites for anionic salts of the biological agent. In one specific example of this aspect, the polymer and/or copolymer includes one or more amine groups and the like. In still another embodiment, the polymer and/or copolymer includes one or more hydrophobic and/or hydrophilic groups. As can be appreciated, the polymer and/or copolymer can include only hydrophobic groups, only hydrophilic groups, or include a combination hydrophobic groups and hydrophilic groups. Furthermore, it can be appreciated that the hydrophobic and/or hydrophilic groups in the polymer and/or copolymer can be the same or different. Nonlimiting examples of hydrophilic groups include carboxylate groups (e.g. acrylate groups, methacrylate groups), alcohol groups, sulfate groups, and the like. Specific non-limiting examples include acrylic acid groups, methacrylic acid groups, and/or maleic acid groups. Nonlimiting examples of hydrophobic groups include ethylene groups, vinyl groups, styrene groups, propylene groups, urethane groups, ester groups, and/or alkyl groups. Specific non-limiting examples include ethylene groups, propylene groups, acrylonitrile groups, and/or methyl methacrylate groups. In still another embodiment, the general formula of the polymer and/or copolymer that can be used is set forth in the following formula:

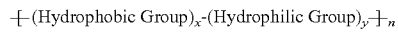

$$\text{+(Hydrophobic Group)}_x\text{-(Hydrophilic Group)}_y\text{+}_n$$

wherein x is the number of hydrophobic monomer units, y is the number of hydrophilic monomer units, and n is the total number of all monomer units in the polymer/copolymer chain. The x and y values can stay constant or vary throughout the polymer/copolymer chain. In addition, the type of hydrophobic monomer or hydrophilic monomer can stay constant or vary throughout the polymer/copolymer chain. Biological agents that form anionic or cationic salts generally bond with the hydrophilic groups in the polymer and/or copolymer chain. Consequently, the more hydrophilic groups in the polymer and/or copolymer chain, the higher the concentration of biological agents that can bond with the polymer and/or copolymer chain. As can be appreciated, one or more biological agents may bond with hydrophobic groups. Therefore, the more hydrophobic groups in the polymer and/or copolymer chain, the higher the concentration of biological agent that can bond with the polymer and/or copolymer chain. Irrespective of whether a biological agent bonds with a hydrophobic group or hydrophilic group, the ratio of the hydrophilic groups to the hydrophobic groups in the polymer and/or copolymer determines the amount of biological agent that bonds with the polymer and/or copolymer. The number of groups of hydrophilic groups (y) and hydrophobic groups (x) typically varies from about 50 to over 10,000. Nonlimiting examples of polymer and/or copolymers that can be used include poly(ethylene terephthalate); polyacetal; poly(lactic acid); polyglycolic acid; polyesters; hydrogels; polytetrafluoroethylene; fluorosilicones hyaluronates; polymethylmethacrylate; poly(ethylene oxide)/poly(butylene terephthalate) co-polymer; polycaprolactone; poly(lactide-co-glycolide); poly(hydroxybutyrate); poly(hydroxybutyrate-co-valerate); polydioxanone; polyorthoester; polyanhydride; poly(glycolic acid); copolymers of lactic acid and glycolic acid; poly(caprolactone); poly(valerolactone); poly(anhydrides); copolymers of poly(caprolactone) or poly(lactic acid) with polyethylene glycol; poly(glycolic acid-co-trimethylene carbonate); polyphosphoester; polyphosphoester urethane; poly(amino acids); cyanoacrylates; poly(trimethylene carbonate); polyvinyl alcohol; polyethylene; poly(iminocarbonate); polyorthoesters; polyacetals; polyorthocarbonates; copoly(ether-esters) (e.g. PEO/PLA); polyalkylene oxalates; polyphosphazenes; biomolecules such as fibrin, fibrinogen, cellulose, starch, collagen and hyaluronic acid; silicones; polyolefins; polyisobutylene and ethylene-alphaolefin copolymers; acrylic polymers and copolymers; vinyl halide polymers and copolymers (e.g. polyvinyl chloride); polyvinyl ethers (e.g. polyvinyl methyl ether); polyvinylidene halides (e.g. polyvinylidene fluoride, polyvinylidene chloride); polyacrylonitrile; polyvinyl ketones; polyvinyl aromatics (e.g. polystyrene); polyvinyl esters (e.g. polyvinyl acetate); copolymers of vinyl monomers; olefins (e.g. ethylene-methyl methacrylate copolymers); acrylonitrile-styrene copolymers; ABS resins; ethylene-vinyl acetate copolymers; polyamides (e.g. Nylon 66, polycaprolactam); alkyd resins; polycarbonates; polyoxymethylenes; polyimides; polyethers; epoxy resins; polyurethanes; rayon; rayon-triacetate; albumin; gelatin; starch; dextrans; polysaccharides; fibrinogen; poly(hydroxybutyrate); poly (alkylcarbonate); poly(orthoesters); EVA copolymers; silicone rubber; poly(methylmethacrylate); cellulose acetate; cellulose butyrate; cellulose acetate butyrate; cellophane; cellulose nitrate; cellulose propionate; cellulose ethers; and/or carboxymethyl cellulose. One particular nonlimiting copolymer chain that can be used to form a polymer salt complex with a biological agent such as, but not limited to, Trapidil, is an ethylene-acrylic acid copolymer. In this copolymer, ethylene is the hydrophobic group and acrylic acid is the hydrophilic group. The mole ratio of the ethylene to the acrylic acid in the copolymer determines the hydrophobicity of the copolymer. Generally a mole ratio for hydrophobic groups/hydrophilic groups ranges from about 90:10-2:98; however, other mole ratios can be used. As can be appreciated, a mole ratio of 2:98 forms a hydrophilic copolymer and a mole ratio of 90:10 forms a hydrophobic copolymer.

In still a further another and/or alternative feature of the present invention, the amount of biological agent that can be loaded on the polymer/copolymer is dependant on the structure of the polymer/copolymer. For biological agents that are cationic, the concentration of biological agent that can be loaded on the polymer/copolymer is a function of the concentration of anionic groups in the polymer/copolymer. Alternatively, for biological agents that are anionic, the concentration of biological agent that can be loaded on the polymer/copolymer is a function of the concentration of cationic groups (e.g. amine groups and the like) in the polymer/copolymer. For instance, when the biological agent is such as, but not limited to, Tripidil, the maximum concentration of Tripidil that can be loaded on to the polymer/copolymer is dependent on the concentration of anionic groups (i.e. carboxylate groups, phosphate groups, sulfate groups, and/or other organic anion groups) in the polymer/copolymer, and the fraction of these anionic groups that can ionically bind the cationic form of Tripidil. As a result, the concentration of biological agent bound to the polymer/copolymer can be varied by controlling the amount of hydrophobic and hydrophilic monomer in the polymer/copolymer, by controlling the efficiency of salt formation between the biological agent, and/or the anionic/cationic groups in the polymer/copolymer. Loading levels of the biological agent in the polymer/copolymer can be from zero to about 90 percent on a weight by weight basis. Therefore, the chemical properties of the biological agent typically dictates the type of polymer/copolymer to be used so as to deliver the desired levels of biological agent into a body cavity to achieve a desired biological response.

Yet a further another and/or alternative feature of the present invention is that the stent is at least partially coated and/or impregnated with one or more coating compounds that includes one or more biological agents, wherein the one or more coating compounds are cross-linked to alter the rate of release of the one or more biological agents into the body passageway or other body parts. It has been discovered that by causing the one or more coating compounds to cross-link after being at least partially coated and/or impregnated onto the stent, the rate at which the one or more biological agents disassociates from the stent and migrates into the body passageway can be controlled. As can be appreciated, the cross-linking of the encapsulated biological agents can be used to alter the rate of release of the one or more biological agents into the body passageway or other body parts. The cross-linking can be instituted by a number to techniques including, but not limited to, using catalysts, using radiation, using heat, and/or the like. In one embodiment, the coating compound is exposed to radiation to cause one or more cross-links to be formed. The radiation can include, but is not limited to, gamma radiation, beta radiation and/or e-beam radiation. When the polymer is exposed to radiation, one or more hydrogen radicals are removed from the polymer and/or copolymer chain. The removal of the hydrogen radical causes the polymer and/or copolymer chain to cross-link with another portion of the polymer and/or copolymer chain or cross-link with a different polymer and/or copolymer. The cross-linking effect results in the salt of the biological agents to become partially or fully entrapped within the cross-linked coating. The entrapped biological agent takes longer to release itself from the cross-linked coating compound and to pass into the body passageway. As a result, the amount of biological agent, and/or the rate at which the biological agent is released from the stent over time can be controlled by the amount of cross-linking in the coating compound. The amount of cross-linking in the coating compound is controlled by the type and amount of radiation applied to the coating compound. Gamma radiation is a higher intensity radiation and e-beam radiation is a lower intensity radiation. Increased radiation intensities and increased radiation exposure periods typically result in increased cross-linking of the coating compound. Each polymer composition has its unique threshold and capacity for cross-linking. The amount of cross-linking that is induced by radiation will be dependent on the chemical structure and composition of the polymer/copolymer. The extent or degree of cross-linking for each polymer/copolymer in combination with the biological agent will vary, depending on the type, strength and duration of radiation, the chemical structure of the biological agent, the type of polymer/copolymer, and the amount of loading (weight percent) of the biological agent in the polymer/copolymer. Reduced solubility of the copolymer/polymer in a body passageway can reduce the need for induced cross-linking of the polymer/copolymer. For instance, while the polymer/copolymer may be hydrophilic, salt formation with a hydrophobic biological agent can result in a reduction of solubility of the bound polymer/copolymer in physiological environments. The reduction in solubility of the bound polymer/copolymer may reduce the need or totally obviate the need for induced cross-linking by radiation or otherwise. The hydrophobic nature of the bound polymer/copolymer will control the rate of release of the biological agent from the polymer/copolymer. The amount of radiation exposure to the coating compound and the biological agent is limited so as to prevent degradation of the biological agent, and/or the coating compound during the irradiation procedure. Generally, less than about 2000 rads (irradiation absorbed doses) are applied to the coating compound, the biological agent, and typically less than about 1000 rads, and more typically less than about 500 rads, and even more typically less than about 400 rads. Generally, at least about 0.1 rad is applied to the coating compound, the biological agent, and typically at least about 1 rad, and more typically at least about 10 rads.

Still yet a further another and/or alternative feature of the present invention is that the stent is at least partially sterilized by subjecting the stent to radiation. Prior to the stent being inserted into a body passageway, the stent should be free or substantially free of foreign organisms so as to avoid infection in the body cavity. In the past, the stent was sterilized by ethylene oxide. Although this compound effectively sterilized the stent, the FDA has imposed various restrictions on this compound making it less desirable to use. Stent sterilization by radiation overcomes the problems and limitations associated with the use of ethylene oxide. The radiation destroys most, if not all, of the foreign organisms on the stent. As a result, sterilization by radiation reduces the occurrence of infection by foreign organisms as compared to past sterilization techniques. Generally, less than about 5000 rads (irradiation absorbed doses) are applied to the stent to at least partially sterilize the stent, and typically less than about 1000 rads, and more typically less than about 500 rads. Generally, at least about 0.1 rad is applied to the stent, and typically at least about 1 rad, and more typically at least about 5 rads.

These and other advantages will become apparent to those skilled in the art upon the reading and following of this description taken together with the accompanied drawings.

BRIEF DESCRIPTION OF THE DRAWINGS

Reference may now be made to the drawings, which illustrate various embodiments that the invention may take in physical form and in certain parts and arrangements of parts wherein:

FIG. 1 is a perspective view of a section of an unexpanded stent which permits delivery of the stent into a body passageway;

FIG. 1A is an enlarged perspective view of one end of the stent of FIG. 1;

FIG. 2 is a perspective view of a section of the unexpanded stent of FIG. 1 in a non-tubular state;

FIG. 3 is a sectional view of the unexpanded stent of FIG. 2 showing a connector used to connect the ends of two tubular body members of the stent;

DETAILED DESCRIPTION OF THE INVENTION

Figure 3B:
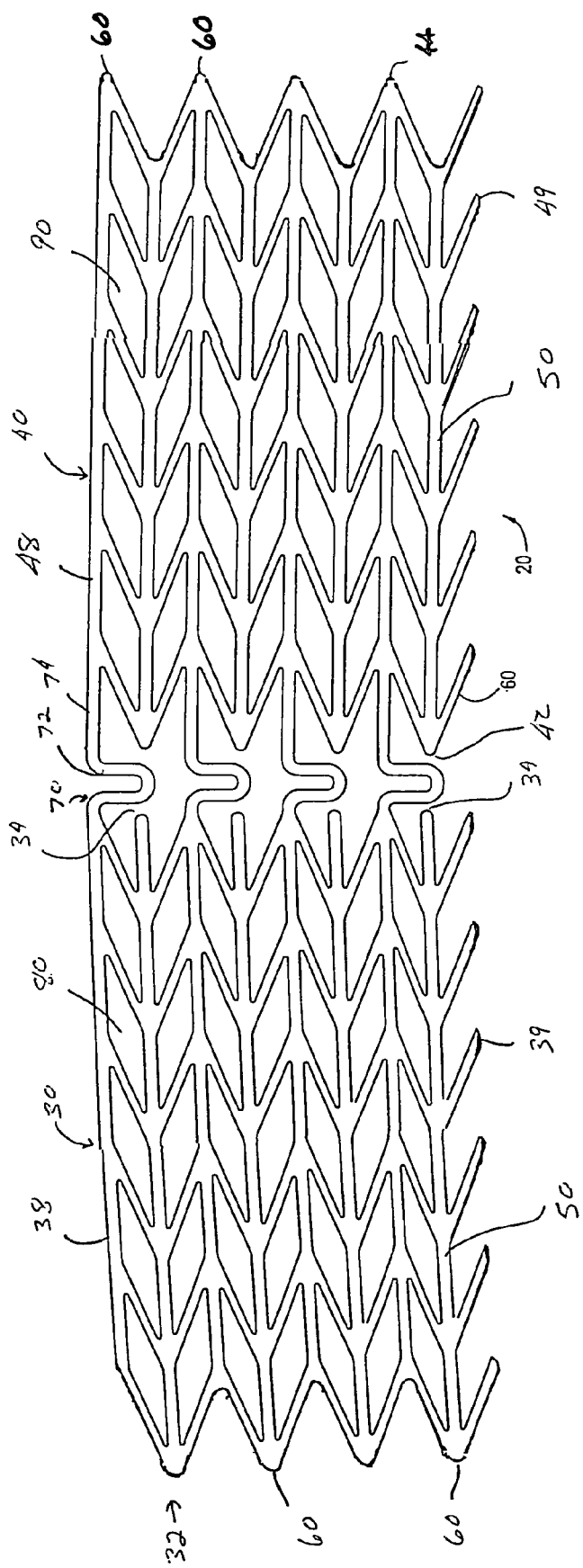
FIG. 3B is a perspective view of the stent of FIG. 1 in a non-tubular state wherein the stent has rounded edges.

Referring now to the drawings wherein the showing is for the purpose of illustrating preferred embodiments of the invention only and not for the purpose of limiting the same, FIGS. 1-8 disclose a stent for a body passageway. The apparatus and structures of the present invention may be utilized not only in connection with an expandable stent for at least partially expanding occluded segments of a body passageway, but also for additional uses. For example, the expandable stent may be used for, but not limited to, such purposes as 1) a supportive stent placement within a blocked vasculature opened by transluminal recanalization, which are likely to collapse in the absence of an internal support; 2) forming a catheter passage through mediastinal and/or other veins occluded by inoperable cancers; 3) reinforcement of catheter created intrahepatic communications between portal and/or hepatic veins in patients suffering from portal hypertension; 4) supportive stent placement of narrowing of the esophagus, the intestine, the ureter and/or the urethra; and/or 5) supportive stent reinforcement of reopened and previously obstructed bile ducts. Accordingly, use of the term "stent" encompasses the foregoing usages within various types of body passageways, and also encompasses use for expanding a body passageway.

The expandable stent 20, as shown in FIGS. 1, 1A, 2, 3, 3B, and 4, generally comprises a two tubular shaped body members 30, 40, each having a first end 32, 42, a second end 34, 44, and a wall surface 36, 46 disposed between the first and second ends. The wall surface is formed by a plurality of intersecting elongated members 50, with at least some of the elongated members intersecting with one another intermediate the first and second ends of each body member. As can be appreciated, the stent can be formed of only one body member or be formed by more than two body members. Body members 30, 40 each have a first diameter which permits delivery of the body members into a body passageway. As shown in FIG. 1, the two body members have substantially the same first diameter. In addition, FIG. 1 discloses that the first diameter of each body member is substantially constant along the longitudinal length of the two body members. As can be appreciated, the diameter of the two body members can differ, and in addition or alternatively, one or both of the body members can have a varying first diameter along at least a portion of the longitudinal length of the body member. Body members 30, 40 each have a second expanded diameter. The second diameter typically varies in size; however, the second diameter can be non-variable in size.

Elongated members 50, which form wall surface 36, 46 of body members 30, 40, can be any suitable material which is compatible with the human body and the bodily fluids with which the stent may come into contact. Typically, the elongated members are made of a material, include a material, and/or are coated with a material readily visible in vivo under fluoroscopic view. The elongated members also are made of a material which has the requisite strength and elasticity characteristics to permit the body members to be expanded from their original cross-sectional size to their expanded cross-sectional size and to further permit the body members to retain their expanded configuration with the enlarged cross-sectional size. Suitable materials for the fabrication of the body members of the stent include, but are not limited to, collagen, gold; platinum; platinum-iridium alloy; alloys of cobalt, nickel, chromium and molybdenum; stainless steel; tantalum; titanium; nickel-titanium alloy; and/or any suitable polymer and/or copolymer material (e.g. poly(L-lactide), poly(D,L-lactide), poly(glycolide), poly(L-lactide-co-D,L-lactide), poly(L-lactide-co-glycolide), poly(D,L-lactide-co-glycolide), poly(glycolide-co-trimethylene carbonate), polydioxanone, polyethylene oxide, polycaprolactone, polyhydroxybutyrate, poly(phosphazene), poly(D,L-lactide-co-caprolactone), poly(glycolide-co-caprolactone), poly (phosphate ester), polyanhydrides, poly(ortho esters), poly (phosphate ester), poly(amino acid), polyacrylate, polyacrylamide, poly(hydroxyethyl methacrylate), elastin polypeptide co-polymer, polyurethane, polysiloxane and their copolymers) having the requisite characteristics previously described. Typically, the one or more body members are primarily made of stainless steel.

Elongated members 50 are generally small diameter wires or bars that have a maximum cross-sectional length or diameter of up to about 0.02 inches, and generally about 0.0005 to 0.008 inch, and typically about 0.002 to 0.004 inch; however, other cross-sectional lengths or diameters can be used. The cross-sectional length or diameter of the elongated members is designated by "a" in FIG. 2. It should, of course, be understood that each elongated member can have a variety of different cross-sectional configurations along part, or the complete length of, each elongated member. Such configurations include circular, oval, elliptical, diamond, triangular, trapezoidal, polygonal (e.g. square, rectangular, hexagonal, etc.).

In addition, the cross-sectional length or diameter of the elongated members can be the same or different.

Referring to FIGS. 1, 2, 3B, and 4, the elongated members on body members 30, 40 are arranged so as to form a plurality of polygonal shapes such as, but not limited to parallelogram shapes 80, 90. The parallelogram pattern is such that similarly oriented parallelograms are aligned on substantially the same longitudinal axis of the body member. This pattern is best shown in FIGS. 2 and 3B. Referring now to FIG. 2, each parallelogram 80, 90 is formed by four sides 82$a$, 82$b$, 82$c$, 82$d$, 92$a$, 92$b$, 92$c$, 92$d$. As shown in FIG. 2, a set of parallelogram shapes are aligned along a single longitudinal axis of body member 30 which are defined by sides 82$a$-$d$, sides 82$a$ of each parallelogram of body member 30 substantially lie in a single longitudinal axis. Likewise, sides 82$c$ of each parallelogram of body member 30 substantially lie in a single longitudinal axis. In addition, sides 82$a$ and 82$c$ of each parallelogram are substantially parallel to each other. Sides 82$b$ and 82$d$ of each parallelogram are substantially parallel to one another. Sides 82$b$ and 82$d$ are shown to slope from left to right. The slope angle between sides 82$b$ and 82$c$ and sides 82$a$ and 82$d$ ranges between 0-90°, and typically about 10-60°. The parallelogram shape has a height "b." Height b will vary depending or the size of the unexpanded body member. The maximum of height "b" is about 1 inch, and generally about 0.005 to 0.5 inch, and typically about 0.01 to 0.1 inch; however, other heights can be used. Sides 82$a$ and 82$c$ can have the same or different length from sides 82$b$ and 82$d$. The length of the sides can be up to 2 inches, and generally ranges from 0.005 to 1 inch, and typically 0.01 to 0.5 inch. As shown in FIG. 2, all the sides have substantially the same length. Each of the parallelograms has substantially the same dimensions.

Referring now to a set of parallelogram shapes aligned along a longitudinal axis of body member 30 which are defined by sides 82$a'$-$d'$, sides 82$a'$ of each parallelogram of body member 30 substantially lie in a single longitudinal axis. Likewise, sides 82$c'$ of each parallelogram of body member 30 substantially lie in a single longitudinal axis. In addition, sides 82$a'$ and 82$c'$ of each parallelogram are substantially parallel to each other. Sides 82$b'$ and 82$d'$ of each parallelogram are substantially parallel to one another. Sides 82$b'$ and 82$d'$ are shown to slope from right to left. The slope angle between sides 82$b'$ and 82$c'$ and sides 82$a'$ and 82$d'$ ranges between 0-90°, and typically about 10-60°. The parallelogram shape has a height "b'." Height b' will vary depending or the size of the unexpanded body member. The height ranges of b' are generally the same as b. The length ranges of sides 82$a$-$d$ are also generally the same as 82$a'$-$d'$. As shown in FIG. 2, all the sides have substantially the same length. Each of the parallelograms has substantially the same dimensions. In addition, the shape and size of the parallelograms is substantially the same as the parallelogram defined by sides 82$a$-$d$. As shown in FIG. 2, the orientation of the parallelograms alternates along the latitudinal axis from parallelograms having sides 82$b$ and 82$d$ sloping from left to right and parallelograms having sides 82$b'$ and 82$d'$ sloping from right to left. A similar parallelogram pattern exists on body member 40. As shown in FIGS. 2 and 3B, the orientation of the parallelograms that are aligned along the same longitudinal axis for body members 30 and 40 is substantially the same. As can be appreciated, this parallelogram pattern allows the body members to be expanded without the body members having a reduction in length in the longitudinal direction. Since a parallelogram is a four sided figure with opposite sides being parallel, the longitudinal axis of structure of body members 30, 40 remains substantially the same during the expansion of the body members. As can be appreciated, the orientation of the parallelograms on one or more body members of the stent can be patterned differently so long as the longitudinal length of the body member remains substantially the same during the expansion of the body member. The symmetrical orientation of the parallelogram pattern on the body members illustrated in FIGS. 1, 2, and 3B results in more uniform expansion of the stent when in the body passageway. In one specific design of a stent to be used in a blood vessel, the cross-sectional length or diameter of the elongated members are substantially uniform and about 0.0025 to 0.0035 inch, the size of the parallelograms in the two body members are substantially the same, the heights b and b' of the parallelograms are substantially the same and are about 0.015 to 0.025 inch, the lengths of the sides of each parallelogram are substantially the same and are about 0.03 to 0.08 inch, and the slope angles of the sides of the parallelograms are about 15-40°.

To provide flexibility to the stent, body members 30, 40 are connected together by a several connector members 70. One such connector member is a connector member having a "U" shaped member 72 as shown in FIGS. 1, 2 and 3. As best shown in FIGS. 1 and 2, connector member 70 joins end 34 of body member 30 to end 42 of body member 40. Four connector members are shown to connect the two body members together. Connector member 70 also includes a bar member 74. The bar member spans between the second end of "U" shaped member 72 and end 42 of body member 40. The first end of "U" shaped member 72 is connected to end 34 of body member 30. As best shown in FIG. 2, connectors 70 do not connect to all of the ends 34 of body member 30 or all of the ends 42 of body member 40. Referring to FIG. 3, the connector member has certain dimensions that enhance the flexibility of the stent. The cross-sectional length or diameter of the "U" shaped member is generally the same as the cross-sectional length or diameter "a" of the elongated members; however, other cross-sectional lengths or diameters of the "U" shaped member can be used. The height of the legs of the "U" shaped member is generally equal to 2a+(b or b') wherein "a" is the cross-sectional length or diameter of the elongated members and b or b' is the height of the parallelograms in the unexpanded state. As can be appreciated, other heights of the legs of the "U" shaped member can be used. The width "c" of the "U" shaped member also affects the flexibility of the connector member and the stent. The width generally is about 1-4 times the cross-sectional length or diameter "a" of the "U" shaped member, and typically about 1.2-2 times the cross-sectional length or diameter "a" of the "U" shaped member; however, other widths can be used. In addition, the spacing of the "U" shaped member from ends 34 of body member 30 and end 42 of body member 40 also affects the flexibility of the connector member and the stent. As shown in FIG. 2, the "U" shaped portion of the connector member is spaced a distance from the ends of the body members that is substantially equal to cross-sectional length or diameter "a" of the elongated members. Bar member 74 has a sufficient length to form the desired spacing of the "U" shaped portion of the connector member from ends of body member 40. The connector member allows the body members to transverse, bend and improve flexibility invariant to the plane of bending. As can be appreciated, other shaped connectors which include an arcuate portion can be used.

Referring now to FIG. 1A, ends 32, 34, 42, and 44 are treated so as to have generally smooth surfaces 60. Generally, the ends are treated by filing, buffing, polishing, grinding, and/or the like of the end surfaces. As a result, sharp edges, pointed surfaces and the like are substantially eliminated from the end section. Typically all the ends of the body members are treated to have smooth surfaces. The smooth surfaces of the ends reduce damage to surrounding tissue as the body member is positioned in and/or expanded in a body passageway. In addition to the ends having generally smooth surfaces, the elongated members 50 and/or joints between the elongated members are formed, filed, buffed, ground, polished, and/or the like to also have generally smooth surfaces. Furthermore, connector members 70 and/or the connection points between the connector members and the elongated members are formed, filed, buffed, ground, polished, and/or the like to have generally smooth surfaces. The substantial removal of sharp edges, pointed surfaces and the like from the entire stent reduces damage to surrounding tissue as the stent is positioned in and/or expanded in a body passageway. As can be appreciated, the ends of the body members, the elongated members, the joints between the elongated members, the connector members, and/or the connection points between the elongated members and the connector members can additionally or alternatively be coated with a material that reduces or eliminates any sharp and/or rough surfaces. The coating, if used, is generally a polymer and/or copolymer material. The coating can be non-biodegradable, biodegradable or semi-biodegradable. Typically the coating thickness is less than the cross-sectional thickness of the elongated members. One non-limiting example of a coating thickness is about 0.00005 to 0.0005 inches.

Elongated members 50 and/or connector members 70 can be formed by a variety of processes. Typically, the elongated members and connector members are formed by etching, laser cutting and/or punching a single piece of material so that the individual intersections of the elongated members and/or the connections between the elongated members and the connector members need not be welded, soldered, glued or otherwise connected together. For example, the stent can be formed from a thin-walled metal tube, and the openings between the elongated members and the connector members are formed by an etching process, such as electromechanical or laser etching, whereby the resultant structure is a stent having a plurality of intersecting elongated members and connector members as shown in FIG. 1. This technique enhances the structural integrity of the structure and reduces the number of rough surfaces at the intersection points. An alternative method or process to form the stent is to use a flat piece of material and form the openings between the elongated members and the connector members by an etching process, such as electromechanical or laser etching, stamping, laser cutting, drilling, and/or the like. Such a flat piece of material is illustrated in FIGS. 3 and 3B. Referring specifically to FIG. 3B, the complete stent with the cut out regions is shown prior to the stent being formed into a tubular shape or some other cross-sectional shape. The flat sheet includes seven (7) formed parallelograms along the latitudinal axis of the sheet and one partially formed parallelogram. The flat sheet also includes ten (10) parallelograms along the longitudinal axis of the sheet. Four "U" shaped connector members are formed along the latitudinal axis of the sheet. The connector members divide the parallelograms along the longitudinal axis of the sheet into two sets of five (5), thus each body member has five (5) parallelograms along the longitudinal axis and seven (7) fully formed parallelograms and one partially formed parallelogram along the latitudinal axis. As shown in FIG. 3B, body members 30, 40 each have an elongated top bar 38, 48. In addition, body members 30, 40 each have a plurality of ends 39, 49 formed from sides 82b', 82d', 92b', and 92d' that are not connected to sides 82c' and 92c' respectively. When the flat sheet is formed into a tubular shape or some other cross-sectional shape, ends 39, 49 are connected to top bar 38, 48 thereby resulting in a fully formed parallelogram, thereby resulting in eight (8) fully formed parallelograms about the outer surface of body members 30, 40. Typically, the flat sheet is designed so as to form an even number of fully formed parallelograms about the outer surface of body members 30, 40. This even number of formed parallelograms facilitates in the desired expansion of the stent in the body passageway. The connections between ends 39, 49 and top bar 38, 48 can be formed by welding, soldering, brazing, adhesives, lock and groove configurations, snap configurations, melting together the ends and the top bars, and the like. Typically, after the connection has been made, the surfaces around the connection are smoothed to remove sharp and/or rough surfaces. FIG. 3B illustrates ends 32, 34, 42, and 44 as being smooth surfaces. Ends 39 are also shown as being relatively smooth surfaces.

Figure 4:
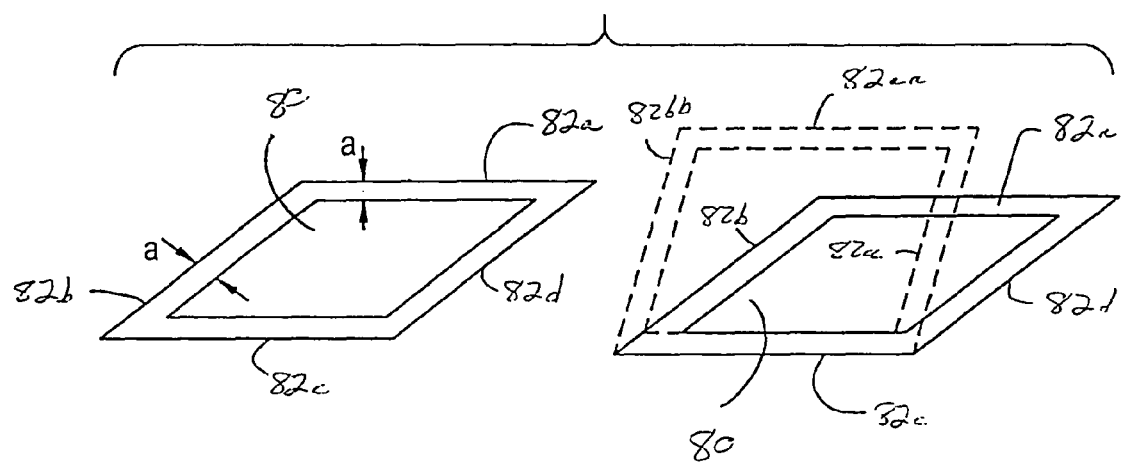
FIG. 4 is a sectional view of the stent of FIG. 2 showing the polygonal structure of the stent before and after expansion.

Referring now to FIG. 4, there is shown a single parallelogram shape 80. The left parallelogram shape is representative of the parallelogram shapes in body members 30, 40 when the stent is in an unexpanded configuration. The length of the sides of the parallelogram are illustrated as being generally the same, thereby forming a rhombus. The angle between sides 82b and 82c and sides 82a and 82d is about 15-30°. When the stent is expanded, the parallelogram shape deforms thereby causing the angle between sides 82b and 82c and sides 82a and 82d to increase. A fully expanded stent would result in the angle between sides 82b and 82c and sides 82a and 82d to be about 90° thereby causing the parallelogram to form into a square or rectangle. Generally, the stent is not fully expanded, thus an angle of less than 90° is formed between sides 82b and 82c and sides 82a and 82d. The right side dashed parallelogram illustrates the typically expanded configuration of the parallelogram. In the expanded state, the angle between sides 82bb and 82cc and sides 82aa and 82dd generally remain the same and generally range between about 60-90°, and typically about 65-80°.

Figure 7:
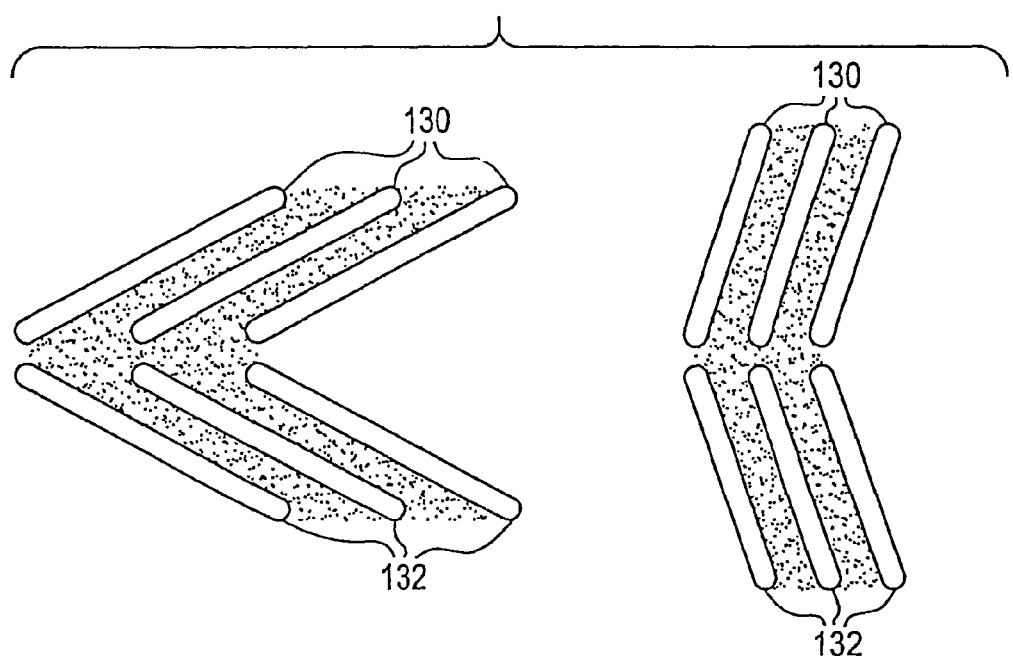
FIG. 7 is a sectional view of the stent of FIG. 5 showing a part of the structure of the stent before and after expansion.
Figure 5:
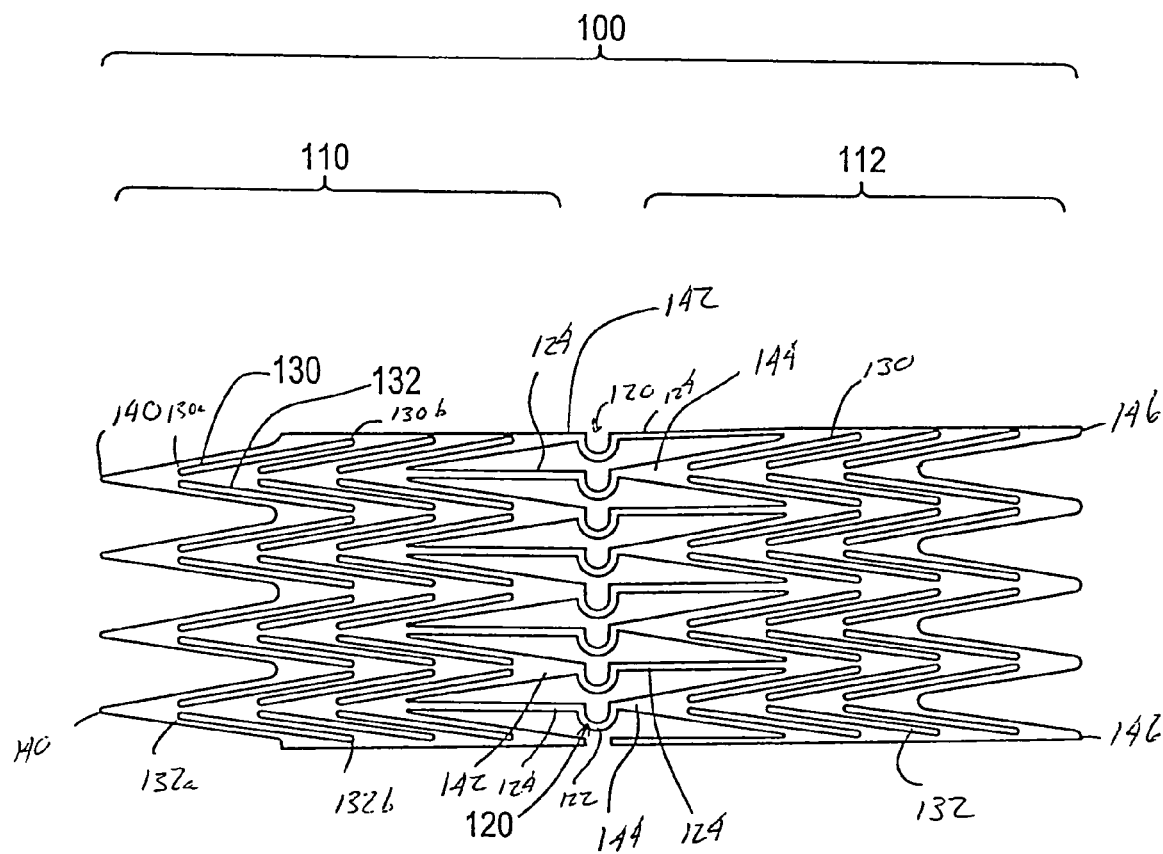
FIG. 5 is a perspective view of an additional embodiment of the present invention showing an unexpanded section of the stent having a series of slots of FIG. 4.
Figure 6:
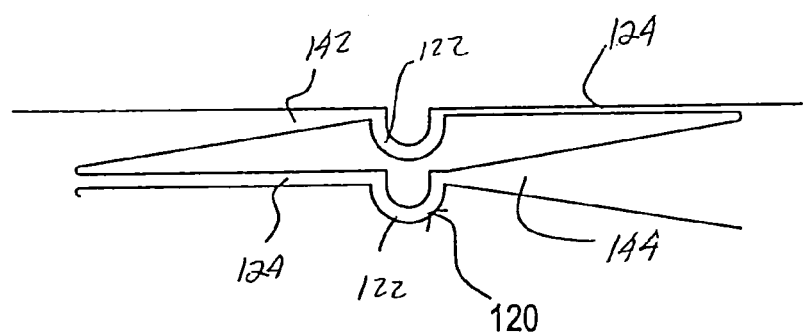
FIG. 6 is a sectional view of the stent of FIG. 5 showing a connector used to connect the ends of two body members of the stent together.

Referring now to FIGS. 5, 6, and 7, a second embodiment of the present invention is illustrated. As shown in FIG. 5, a stent 100 includes two body members 110, 112. As can be appreciated, stent 100 can include more than two body members. Body members 110, 112 include ends 140, 142 of body member 110 and ends 144, 146 of body member 112. The two body members are connected together by several connector members 120. Generally, connector members 120 include an arcuate shaped member 122, and typically is "U" shaped, similar to shape and size of connector members 70 as shown in FIG. 3B. Connector member 120 also includes a bar member 124. The connector members provide flexibility to the stent body members 110, 112. The bar member spans between the second end of "U" shaped member 122 and end. As best shown in FIGS. 5 and 6, the "U" shaped member alternates between being connected to end 142 and end 144 and similarly, the bar member alternates between being connected to end 144 and end 142. The "U" shaped members are typically spaced apart a sufficient distance so as to avoid contacting one another in the unexpanded state. In addition, the "U" shaped members are typically spaced apart a sufficient distance so as to avoid contacting one another in the expanded state. The connector members allow the body members to transverse, bend and improve flexibility invariant to the plane of bending. As can be appreciated, other shaped connectors which include an arcuate portion can be used.

Referring to FIG. 5, body members 110, 112 are substantially symmetrical to one another and typically have substantially identical dimensions. Each body member includes a plurality of slots 130, 132. Slots 130, 132 are generally equal in length and width; however, the width and/or length of the slots can vary. Each slot 130 includes two ends 130a, 130b and each slot 132 includes two ends 132a, 132b. Each series of slots 130 along a longitudinal axis of the stent are arranged substantially parallel to one another. Similarly, each series of slots 132 along a longitudinal axis of the stent are arranged substantially parallel to one another. Slots 130 and 132 that are positioned closest to one another form a series of "V" shapes along a longitudinal axis of the stent. Ends 130a and 132a form the base of the "V" shape. As shown in FIG. 5, four different series of "V" shapes are positioned along a longitudinal axis of the stent. As shown in FIG. 5, all the "V" shapes are symmetrically oriented on each body member. The angle between slots 130 and 132 is between about 0-90°, and generally about 5-60°, and typically about 10-30°. The width of each slot is up to about 0.5 inch, and generally about 0.0005 to 0.25 inch, and typically about 0.001 to 0.1 inch. The length of each slots is up to about 2 inches, and generally about 0.005 to 1 inch, and typically about 0.01 to 0.5 inch. As can be appreciated, the slot arrangement is such that the stent retains its longitudinal length from its unexpanded to its expanded state. The configuration of slots 130, 132 in the pre-expanded and post-expanded position is shown in FIG. 7. The slot configuration in the left figure illustrates the slots in the unexpanded state. The slot configuration in the right figure illustrates the slots in the expanded state. As illustrated in the expanded state, the slots 130 and 132 begin to align and the angle between the slots increases. Generally, the angle between the slots in the expanded state is between about 45-90°, and typically about 60-80°. In one specific design of a stent to be used in a blood vessel, four sets of "V" shaped slots are positioned in each body member and eight connector members are used to connect the two body members together. The length of all the slot members are substantially the same. The angle between slots is about 15-25° in the unexpanded state. The width of each slot is about 0.002-0.007 inch. The length of each slot is 0.05-0.2 inch.

The slots in the body members can be formed in a variety of manners. In one method or process, the stent is formed from a flat piece of material and the slots and connector members are formed by an etching process, such as electromechanical or laser etching, stamping, laser cutting, drilling, and/or the like. After the slots are formed, the stent is generally treated so as to have generally smooth surfaces 60. Generally, the ends, slots and connector members are treated by filing, buffing, polishing, grinding, and/or the like. As a result, sharp edges, pointed surfaces and the like are substantially eliminated. The smooth surfaces reduce damage to surrounding tissue as the body member is positioned in and/or expanded in a body passageway. As can be appreciated, the ends of the body members, the slots, and/or the connector members can additionally or alternatively be coated and/or impregnated with a material that reduces or eliminates any sharp and/or rough surfaces. The coating, if used, is generally a polymer and/or copolymer material. The coating can be non-biodegradable, biodegradable or semi-biodegradable. Typically the coating thickness is less than the half the width of the slots. One non-limiting example of a coating thickness is about 0.00005 to 0.0005 inches. After the flat material has the slots and connector members inserted therein, the flat material is rolled or otherwise formed and the side edges of the flat material are connected together form the stent. The side edges of the flat material can be connected together by a variety of techniques such as, but not limited to, welding, soldering, brazing, adhesives, lock and groove configurations, snap configurations, melting together the edges, and the like. The cross-sectional shape of the stent is typically circular; however, other cross-sectional shapes can be formed such as, but not limited to, oval, elliptical, diamond, triangular, trapezoidal, polygonal (e.g. square, rectangular, hexagonal, etc.). The connection between the edges is generally treated to reduce or eliminate the rough or sharp surfaces.

Figure 8:
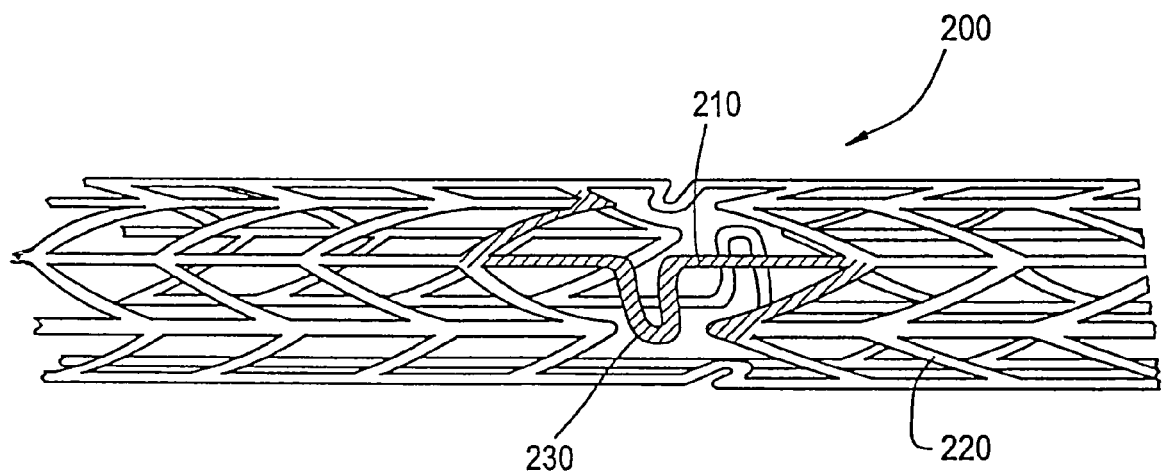
FIG. 8 is a perspective view of a stent of FIG. 1 showing a coating that includes a biological agent on the stent.

Referring now to FIG. 8, a stent 200 is shown to include a compound 210 on the elongated members 220 and connector 230 of the body member. Compound 210 is or includes a vascular active agent that inhibits and/or prevents restenosis, vascular narrowing and/or in-stent restenosis. One preferable compound that is or is included in the vascular active agent is a PDGF inhibitor. One type of PDGF inhibitor that is used is Trapidil; however, other PDGF inhibitors can be used. As can be appreciated, compound 210 can also or alternatively include one or more secondary vascular active agents and/or other biological agents.

The amount of vascular active agent and/or secondary vascular active agent and/or other biological agent delivered to a certain region of a body passageway can be controlled by varying the coating thickness, drug concentration of the vascular active agent and/or secondary vascular active agent and/or other biological agent, the amount of surface area of the body member 200 that is coated and/or impregnated with the vascular active agent and/or secondary vascular active agent and/or other biological agent, and/or the size of cavity openings in the stent. As can be appreciated, the vascular active agent and/or secondary vascular active agent and/or other biological agent can be combined with, or at least partially coated with, another compound that affects the rate at which the vascular active agent and/or secondary vascular active agent and/or other biological agent is released from the surface of the stent. A bonding compound can be used in conjunction with compound 210 to assist in binding compound 210 to body member 200. In addition, or alternatively, the bonding compound can be used to control the release of compound 210 into the body passageways. In one particular application, the bonding compound is biodegradable and dissolves over the course of time. The bonding agent is coated at one or more thicknesses over compound 210 to delay delivery of compound 210 into a body passageway.

Figure 10:
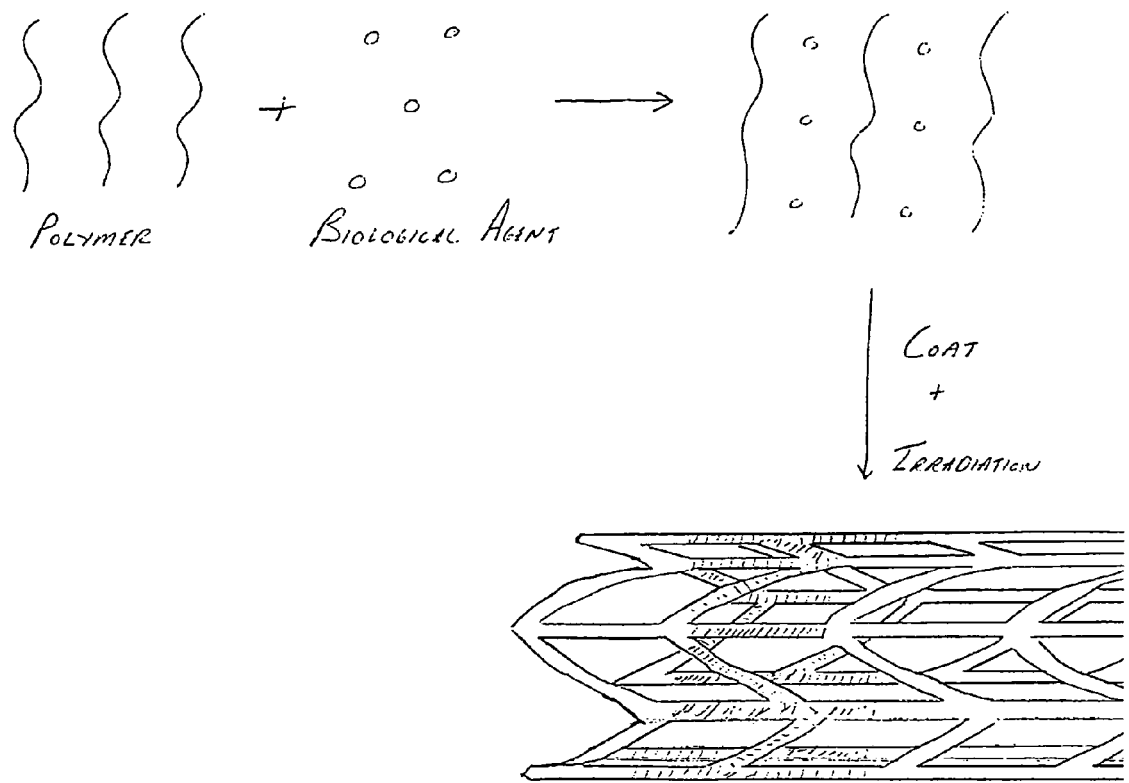
FIG. 10 is a graphical representation of the steps for coating the stent with a biological agent and coating compound.
Figure 10A:
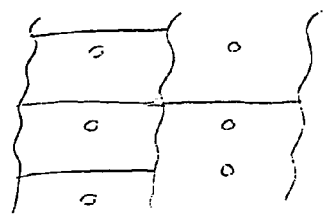
FIG. 10A is a graphical representation of the biological agent entrapped in a cross-linked polymer and/or copolymer; and, FIG. 11 is a graphical representation of the steps to form cross-linking of a polymer and/or copolymer that includes a biological agent.
Figure 11:
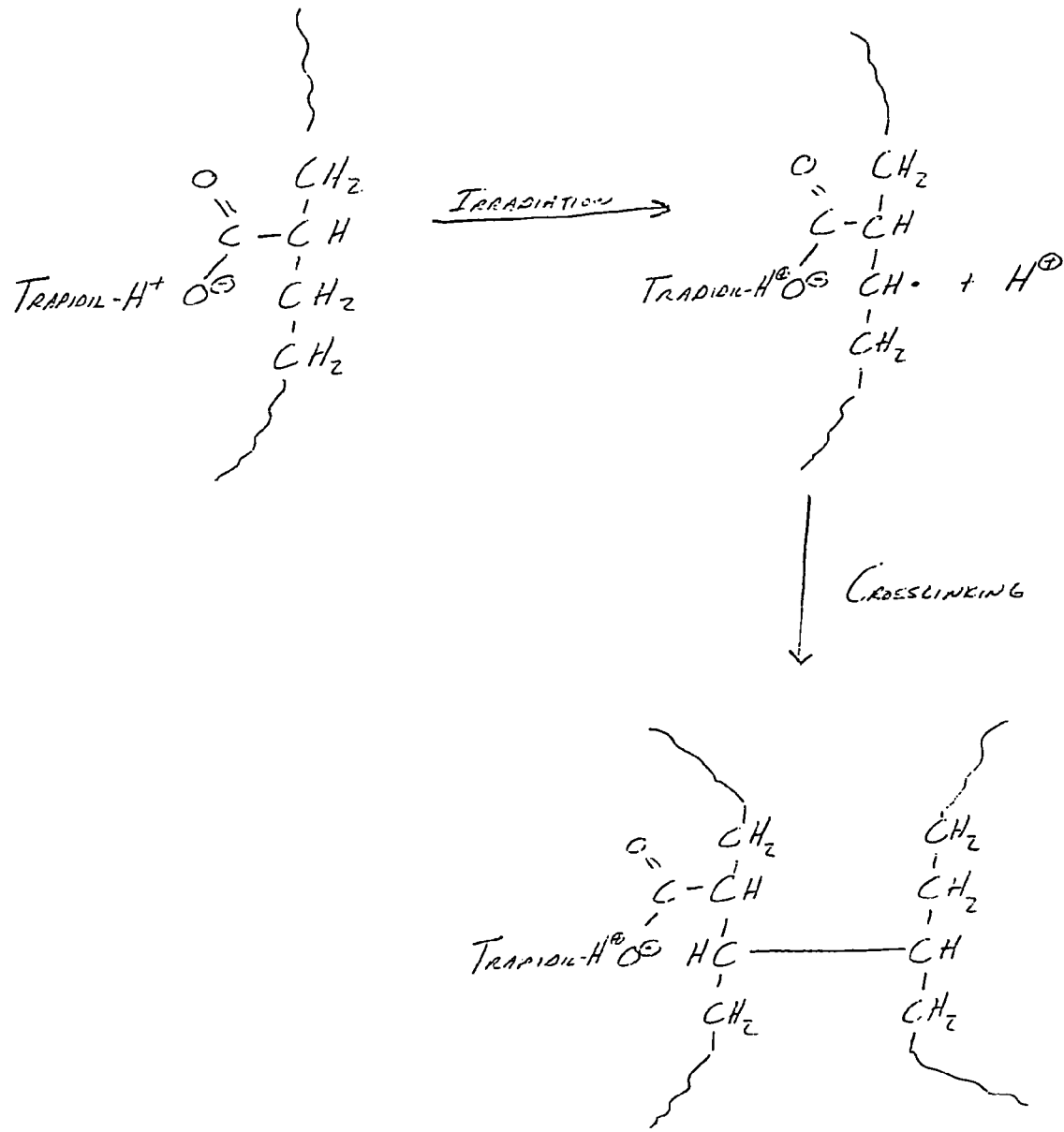

Referring now to FIGS. 10, 10A and 11, the vascular active agent and/or secondary vascular active agent and/or other biological agent is combined with a polymer and/or copolymer prior to being at least partially coated onto the stent. The polymer and/or copolymer can be formulated to bond the vascular active agent and/or secondary vascular active agent and/or other biological agent to the stent; however, the polymer and/or copolymer can be used in combination with other compounds to facilitate in the bonding of the vascular active agent, secondary vascular active agent and/or other biological agent and/or polymer and/or copolymer to the stent. Referring now to FIG. 10, there is illustrated a typical process whereby one or more vascular active agents, one or more secondary vascular active agent, one or more other biological agents, and/or other compounds are coated to the stent. As shown in FIG. 10, the vascular active agent and/or secondary vascular active agent and/or other biological agent is mixed with a polymer and/or copolymer prior to coating the stent. The polymer and/or copolymer is formulated to delay and/or regulate the time and/or amount of vascular active agent and/or secondary vascular active agent and/or other biological agent being released into the body passageway. The polymer and/or copolymer can be a biodegradable compound, a non-biodegradable compound, or a partially biodegradable compound. The polymer and/or copolymer can be formulated so as to form one or more bonds with the vascular active agent and/or secondary vascular active agent and/or other biological agent, or be chemically inert with respect to the vascular active agent and/or secondary vascular active agent and/or other biological agent. Generally, the polymer and/or copolymer form at least one bond with one or more vascular active agents and/or secondary vascular active agents and/or other biological agents. The bond is generally formed in a polymer and/or copolymer salt complex. For example, when the vascular active agent is or includes Trapidil, the Trapidil forms a salt complex with the polymer and/or copolymer. The Trapidil forms the cation component of the salt complex and the polymer and/or copolymer forms the anionic component of the salt complex. Typically, the carboxylate groups, phosphate groups, and/or sulfate groups in the polymer and/or copolymer form the bond with this vascular active agent.

After the vascular active agent and/or secondary vascular active agent and/or other biological agent has been mixed with the polymer and/or copolymer, the mixture is coated onto the stent. After the stent or a portion of the stent has been coated with the mixture, the coated stent can be subjected to radiation. The radiation causes the polymer and/or copolymer to form cross-linking between the polymer and/or copolymer chains. The cross-linking alters the rate of release of the one or more vascular active agents and/or secondary vascular active agents and/or other biological agents into the body passageway. The radiation typically includes, but is not limited to, gamma radiation, beta radiation, and/or e-beam radiation; however, other types of radiation (e.g. inferred, ultraviolet) can be used in conjunction with or as an alternative to gamma radiation, beta radiation, and/or e-beam radiation. When the polymer and/or copolymer is exposed to radiation, one or more hydrogen radicals are typically removed from the polymer and/or copolymer chain. This process is illustrated in FIG. 11. As can be appreciated, other elements in the polymer and/or copolymer can be removed and/or disassociated from the polymer and/or copolymer when the polymer and/or copolymer is exposed to radiation. In FIG. 11, a polymer and/or copolymer chain includes a carboxyl group that has formed a salt complex with Trapidil. Radiation is applied to the polymer and/or copolymer salt complex resulting in removal of one or more hydrogen atoms from the polymer and/or copolymer chain. The removal of the hydrogen radical causes the polymer and/or copolymer chain to cross-link with another portion of the polymer and/or copolymer chain or cross-link with a different polymer and/or copolymer as shown in FIG. 11. FIG. 10A illustrates the vascular active agent and/or secondary vascular active agent and/or other biological agent being entrapped or partially entrapped within the cross-linking of the polymer and/or copolymer. The entrapped vascular active agent and/or secondary vascular active agent and/or other biological agent takes longer to release itself from the cross-linked coating compound and to pass into the body passageway. As a result, the amount of vascular active agent and/or secondary vascular active agent and/or other biological agent, and/or rate at which the vascular active agent and/or secondary vascular active agent and/or other biological agent released from the stent over time can be controlled by the amount of cross-linking in the coating compound. The amount of cross-linking in the coating compound is controlled by the type and amount of radiation applied to the coating compound. The amount of radiation exposure to the polymer and/or copolymer salt complex is controlled so as to prevent degradation of the vascular active agent, secondary vascular active agent, other biological agent, and/or polymer and/or copolymer during the irradiation procedure. In addition to the radiation causing cross-linking, the radiation sterilizes the stent. The radiation destroys most if not all of the foreign organisms on the stent and/or on any coating on the stent. As a result, sterilization by radiation reduces the occurrence of infection by foreign organisms.

Figure 9:
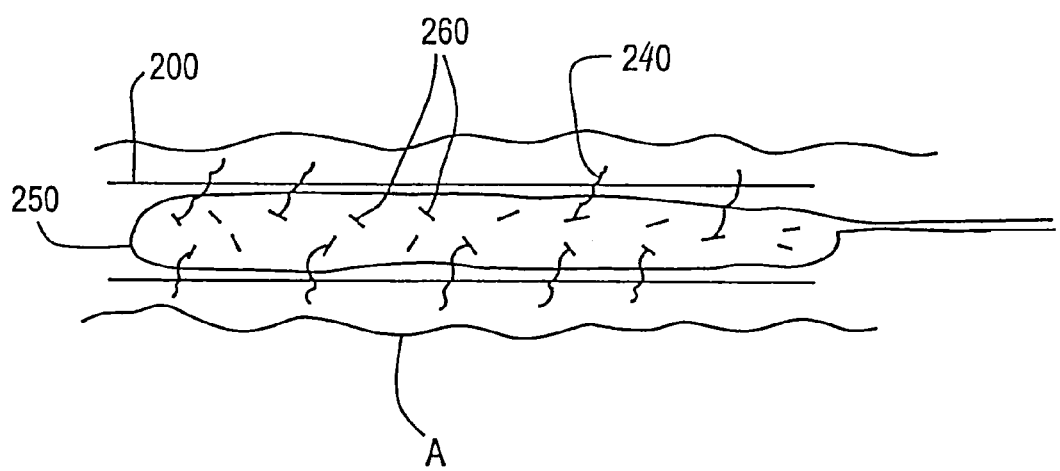
FIG. 9 is a perspective view of an angioplasty balloon delivering fluid materials to a local site.

Referring now to FIG. 9, a vascular active agent and/or secondary vascular active agent and/or other biological agent 240 is delivered into a body passageway A via angioplasty balloon 250. Balloon 250 includes one or more slots 260 to allow delivery of vascular active agent and/or secondary vascular active agent and/or other biological agent 240 into body passageway A. Balloon 250 can be used to both deliver compound 210 and expand the stent 200, or be used in conjunction with another balloon or stent expanding device. When the vascular active agent includes one or more PDGF inhibitors, local delivery of the inhibitor by a stent and/or via a balloon is highly advantageous.

The present invention has been described with reference to a number of different embodiments. It is to be understood that the invention is not limited to the exact details of construction, operation, exact materials or embodiments shown and described, as obvious modifications and equivalents will be apparent to one skilled in the art. It is believed that many modifications and alterations to the embodiments disclosed will readily suggest themselves to those skilled in the art upon reading and understanding the detailed description of the invention. It is intended to include all such modifications and alterations insofar as they come within the scope of the present invention.

What is claimed is:

1. An expandable intraluminal graft for use within a body passageway including a body member, a intermediate compound, and biological agent, said intermediate compound, said at least one biological agent, and mixtures thereof coated on at least a portion of the body member, said body member having first and second ends and a wall surface disposed between said first and second ends defining a longitudinal axis of said body member, said body member having a first cross-sectional shape having a first cross-sectional area which permits intraluminal delivery of said body member into the body cavity, and a second expanded cross-sectional shape having a second cross-sectional area which is greater than said first cross-sectional area, said biological agent at least partially coated on or secured to the surface of said body member, said biological agent including two or more compounds selected from the group consisting of Trapidil, GM-CSF, Taxol, rapamycin, and mixtures thereof, said biological agent including Trapidil, said intermediate compound at least partially securing said biological agent to said body member, said intermediate compound at least partially encapsulating said biological agent in said intermediate compound, and combinations thereof.

2. The expandable intraluminal graft as defined in claim 1, wherein said intermediate compound is at least partially formed of 1) a biodegradable material and forms a polymer salt complex with said biological agent 2) a plurality of radiation induced cross-links that at least partially encapsulate said biological agent in said intermediate compound, or mixture thereof.

3. The expandable intraluminal graft as defined in claim 2, wherein said biological agent includes Trapidil and GM-CSF.

4. The expandable intraluminal graft as defined in claim 3, wherein said biological agent includes Taxol, rapamycin, and mixtures thereof.

5. The expandable intraluminal graft as defined in claim 4, wherein said biological agent is releasably coated on said body member.

6. The expandable intraluminal graft as defined in claim 5, wherein said intermediate compound at least partially delays delivery of said biological agent into said body passageway.

7. The expandable intraluminal graft as defined in claim 6, wherein said intermediate compound includes a polymer, a copolymer or mixtures thereof.

8. The expandable intraluminal graft as defined in claim 7, wherein said intermediate compound includes hydrophobic and hydrophilic compounds.

9. The expandable intraluminal graft as defined in claim 8, wherein said intermediate compound includes an ethylene-acrylic acid copolymer.

10. The expandable intraluminal graft as defined in claim 9, wherein said body member maintains a substantially constant longitudinal length when expanded from said first cross-sectional shape to said second cross-sectional shape.

11. The expandable intraluminal graft as defined in claim 10, wherein said first and second ends having a substantially smooth surface.

12. The expandable intraluminal graft as defined in claim 11, wherein said body member is at least partially coated with a material that is visible under fluoroscopy, said material being coated on an outer surface of said body member and at least one end of said body member.

13. The expandable intraluminal graft as defined in claim 12, wherein said body member is treated with Gamma or Beta radiation to reduce the vascular narrowing of at least a portion of said body cavity.

14. The expandable intraluminal graft as defined in claim 13, including a balloon, said balloon including at least one opening to allow delivery of said biological substance from an interior of said balloon to said body cavity, said biological substance includes at least one of said biological agents.

15. The expandable intraluminal graft as defined in claim 13, wherein at least a portion of said body member is formed of a biodegradable material.

16. The expandable intraluminal graft as defined in claim 5, wherein said intermediate compound includes a polymer, a copolymer or mixtures thereof.

17. The expandable intraluminal graft as defined in claim 16, wherein said intermediate compound includes hydrophobic and hydrophilic compounds.

18. The expandable intraluminal graft as defined in claim 17, wherein said intermediate compound includes an ethylene-acrylic acid copolymer.

19. The expandable intraluminal graft as defined in claim 2, wherein said intermediate compound includes a polymer, a copolymer or mixtures thereof.

20. The expandable intraluminal graft as defined in claim 19, wherein said intermediate compound includes hydrophobic and hydrophilic compounds.

21. The expandable intraluminal graft as defined in claim 20, wherein said intermediate compound includes an ethylene-acrylic acid copolymer.

22. The expandable intraluminal graft as defined in claim 1, wherein said intermediate compound includes a plurality of radiation induced cross-links that at least partially encapsulate said biological agent in said intermediate compound.

23. The expandable intraluminal graft as defined in claim 22, wherein said biological agent includes Trapidil and GM-CSF.

24. The expandable intraluminal graft as defined in claim 23, wherein said biological agent includes Taxol, rapamycin, and mixtures thereof.

25. The expandable intraluminal graft as defined in claim 24, wherein said biological agent is releasably coated on said body member.

26. The expandable intraluminal graft as defined in claim 25, wherein said intermediate compound at least partially delays delivery of said biological agent into said body passageway.

27. The expandable intraluminal graft as defined in claim 26, wherein said body member maintains a substantially constant longitudinal length when expanded from said first cross-sectional shape to said second cross-sectional shape.

28. The expandable intraluminal graft as defined in claim 27, wherein said first and second ends having a substantially smooth surface.

29. The expandable intraluminal graft as defined in claim 28, wherein said body member is at least partially coated with a material that is visible under fluoroscopy, said material being coated on an outer surface of said body member and at least one end of said body member.

30. The expandable intraluminal graft as defined in claim 29, wherein said body member is treated with Gamma or Beta radiation to reduce the vascular narrowing of at least a portion of said body cavity.

31. The expandable intraluminal graft as defined in claim 30, including a balloon, said balloon including at least one opening to allow delivery of said biological substance from an interior of said balloon to said body cavity, said biological substance includes at least one of said biological agents.

32. The expandable intraluminal graft as defined in claim 30, wherein at least a portion of said body member is formed of a biodegradable material.

33. The expandable intraluminal graft as defined in claim 1, wherein said biological agent includes Trapidil and GM-CSF.

34. The expandable intraluminal graft as defined in claim 33, wherein said biological agent includes Taxol, rapamycin, and mixtures thereof.

35. The expandable intraluminal graft as defined in claim 33, wherein said biological agent is releasably coated on said body member.

36. The expandable intraluminal graft as defined in claim 1, wherein said biological agent is releasably coated on said body member.

37. The expandable intraluminal graft as defined in claim 34, wherein said biological agent is releasably coated on said body member.

38. The expandable intraluminal graft as defined in claim 1, wherein said intermediate compound at least partially delays delivery of said biological agent into said body passageway.

39. The expandable intraluminal graft as defined in claim 1, wherein said body member maintains a substantially constant longitudinal length when expanded from said first cross-sectional shape to said second cross-sectional shape.

40. The expandable intraluminal graft as defined in claim 1, wherein said first and second ends having a substantially smooth surface.

41. The expandable intraluminal graft as defined in claim 1, wherein said body member is at least partially coated with a material that is visible under fluoroscopy, said material being coated on an outer surface of said body member and at least one end of said body member.

42. The expandable intraluminal graft as defined in claim 1, wherein said body member is treated with Gamma or Beta radiation to reduce the vascular narrowing of at least a portion of said body cavity.

43. The expandable intraluminal graft as defined in claim 1, including a balloon, said balloon including at least one opening to allow delivery of said biological substance from an interior of said balloon to said body cavity, said biological substance includes at least one of said biological agents.

44. The expandable intraluminal graft as defined in claim 1, wherein at least a portion of said body member is formed of a biodegradable material.

\* \* \* \* \*